(12) United States Patent
Deng et al.

(10) Patent No.: US 7,531,662 B2
(45) Date of Patent: May 12, 2009

(54) CINCHONA-ALKALOID-BASED CATALYSTS, AND ASYMMETRIC ALCOHOLYSIS OF CYCLIC ANHYDRIDES USING THEM

(75) Inventors: Li Deng, Newton Lower Falls, MA (US); Xiaofeng Liu, Waltham, MA (US)

(73) Assignee: Brandeis University, Waltham, MA (US)

( * ) Notice: Subject to any disclaimer, the term of this patent is extended or adjusted under 35 U.S.C. 154(b) by 404 days.

(21) Appl. No.: 10/865,490

(22) Filed: Jun. 10, 2004

(65) Prior Publication Data

US 2005/0043353 A1 Feb. 24, 2005

Related U.S. Application Data

(60) Provisional application No. 60/484,218, filed on Jul. 1, 2003, provisional application No. 60/477,531, filed on Jun. 11, 2003.

(51) Int. Cl.
*C07D 453/04* (2006.01)
*A61K 31/47* (2006.01)

(52) U.S. Cl. ........................ 546/134; 546/135; 546/136; 514/314

(58) Field of Classification Search .................. 560/134, 560/136, 135, 152; 544/128, 237, 238; 514/314
See application file for complete search history.

(56) References Cited

U.S. PATENT DOCUMENTS 2,566,957 A 9/1951 Pedlow et al.
5,198,557 A 3/1993 Giordano et al.

(Continued)

FOREIGN PATENT DOCUMENTS

CA 2329316 11/1990

(Continued)

OTHER PUBLICATIONS

Bolm, C. et al., "Pratical and Highly Enatioselective Ring opening of cyclic Meso-Anhydrides mediated by Cinchona Alkaloids", 2000, Journal of Organic Chemistry, vol. 65, pp. 6985.*

(Continued)

*Primary Examiner*—Porfirio Nazario-Gonzalez
*Assistant Examiner*—Yate' K Cutliff
(74) *Attorney, Agent, or Firm*—Dana M. Gordon; Foley Hoag LLP

(57) ABSTRACT

One aspect of the present invention relates to cinchona-alkaloid-based catalysts. A second aspect of the invention relates to a method of preparing a derivatized cinchona alkaloid catalyst by reacting a cinchona-alkaloid with base and a compound that has a suitable leaving group. Another aspect of the present invention relates to a method of preparing a chiral, non-racemic compound from a prochiral cyclic anhydride or a meso cyclic anhydride, comprising the step of: reacting a prochiral cyclic anhydride or a meso cyclic anhydride with a nucleophile in the presence of a catalyst; wherein said prochiral cyclic anhydride or meso cyclic anhydride comprises an internal plane of symmetry or point of symmetry or both; thereby producing a chiral, non-racemic compound; wherein said catalyst is a derivatized cinchona-alkaloid. Yet another aspect of the present invention relates to a method of kinetic resolution, comprising the step of: reacting a racemic cyclic anhydride with an alcohol in the presence of a derivatized cinchona-alkaloid catalyst.

25 Claims, 29 Drawing Sheets quinidine-based catalysts

| Catalyst | R |
|---|---|
| QD-PH | —CH₂—≡—Ph |
| QD-AN | —CH₂—≡—⟨⟩—OMe |
| QD-NT | —CH₂—≡—⟨⟩—NO₂ |
| QD-AC | -CH₂-C(=O)-CH₃ |
| QD-CH | -CH₂-C(=O)-O-C₆H₁₁ |

U.S. PATENT DOCUMENTS

| | | | | |
|---|---|---|---|---|
| 5,260,461 | A | * | 11/1993 | Hartung et al. ............. 549/447 |
| 5,877,343 | A | | 3/1999 | Mittendorf |
| 5,929,232 | A | | 7/1999 | Jacobsen et al. |
| 7,053,236 | B2 | | 5/2006 | Deng et al. |
| 2005/0154209 | A1 | * | 7/2005 | Ishii et al. .................... 546/134 |

FOREIGN PATENT DOCUMENTS

| | | | |
|---|---|---|---|
| GB | 1045091 | | 10/1966 |
| WO | WO 98/35927 | * | 8/1998 |
| WO | WO 96/28402 | | 2/2000 |
| WO | WO-01/74741 | | 10/2001 |
| WO | WO 02/10096 A1 | | 2/2002 |

OTHER PUBLICATIONS

McDaid, P. et al., "A highly Enantioselective and General conjugated Addition of Thiols to cyclic Enones with an Organic Catalyst", 2002, Agew. chem. Int. Ed., vol. 41, issue No. 2, pp. 338.*

Jacobsen, E. et al. "Kinetic Role of Alkaloid Ligands in Asymmetric Catalytic Dihydroxylation", 1989, Journal of the American Chemical Society, vol. 111, pp. 737.*

Cortez, et al. "Bicyclic beta-lactones viq intramolecular NCAL Reactions with Cinchona Alkaloids: Effect of the C9-Substitutent on Enantioselectivity and Catalyst Conformation", 2001, Synthesis, vol. 11, pp. 1732, 1733.*

Janda et al. PEG-Bound Alkaloid Ligands and use thereof, 1998, Chemical Abstracts, American Chemical Society, Abstract of HCAPLUS, Answer 24, 2 pages+.*

Jacobsen et al. Kinetic Role of the Alkaloid Ligands in Asymmetric Catalytic Dihydroxylation, 1989, Journal of the American Chemical Society, vol. 111, issue 2, pp. 737-739.*

Aitken and Gopal, "Catalytic Asymmetric Ring-openning of Bridged Tricyclic Anhydrides", Tetrahedron Asymmetry 1(8):517-520 (1990).

Aitken et al., "Catalytic asymmetric Synthesis of Highly Functionalised Compounds With Six Contiguous Stereocentre", J. Chem. Soc. Chem. Commun, pp. 632-634 (1988).

Albers et al., "Desymmetrisation of *meso*-Anhydrides Utilising (S)-Proline Derivatives", Synthesis, pp. 393-398 (Mar. 1996).

Aldrich Chemical Company, p. 1165, Item # 13,689-1 (1992).

Becker and Sharpless, "A New Ligand Class for the Asymmetric Dihydroxylation of Olefins", Angew Chem. Int. Ed. Engl., 35(4):448-450 (1996).

Berkowitz et al. "Enzyme-Assisted Asymmetric total Synthesis of (—)—Podophyllotoxin and (—)—Picropodophyllin", J. Org. Chem. 65:847-860 (2000).

Bolm et al., "Simple and Highly Enantioselective Noenzymatic Ring Opening of Cyclic Prochiral Anhydrides", Synlett, No. 2 :195-196 (1999).

Borzilleri and Weinreb, "Total Synthesis of Popuamine via a Stereospecific Intramolecular Imino Ene Reaction of an Allenylsilane", J. Am. Chem. Soc., 116:9789-9790 (1994).

Borzilleri et al., "Total Synthesis of the Unusual Marine Alkaloid (—)—Papuamine Utilizing a Novel Imino Ene Reaction", J. Am. Chem. Soc., 117:10905-10913 (1995).

Brion et al., "Stereoselective Synthesis of a trans-Octahydroindole Derivative. Precursor of Trandolapril (RU 44 570), an Inhibitor of Angiotensin Converting Enzyme", Tetrahedron Letters 33(34):889-4892 (1992).

Burk et al., "Highly Regio- and Enantioselective Catalytic Hydrogenetion of Enamides in Conjugated Diene Systems: Synthesis and Application of γ,δ-Unsaturated Amino Acids", J. Am. Chem. Soc., 120:657-663 (1998).

Burk et al., "Rh-DuPHOS-Catalyzed Enantioselective Hydrogenetion of Enol Esters. Application to the Synthesis of Highly Enantioenriched α-Hydroxy Esters and 1,2-Diols", J. Am. Chem. Soc., 120:4345-4353 (1998).

Casas and Ortuno, "(+)-(1 R, 2S, 3S, 4S)- and (−)- 1S, 2S, 2R, 3R, 4R)-Bicyclo-(2.2.1) heptane-2,3 -dicarboxylic Acid, 2-Methyl Esters. Formal Synthesis of the TXA$_2$ Antagonist S-1452", Abstract, Universidad de Barcelona, pp. 1205-1211 (Jul 23, 1992).

Corey and Grogan, "Enantioselective Synthesis of -Amino Nitriles from N-Benzhydryl Imines and HCN with a Chiral Bicyclic Guanidine as Catalyst", Organic Letters, 1(1):157-160 (1999).

Corey et al., "A Rational Approach of Catalytic Enatioselective Enolate Alkylation Using a Structurally Rigidfied and Defined Chiral Quaternary Ammonium Salt Under Phase Transfer Conditions", J. Am. Chem. Soc., 119:12414-12415 (1997).

Corey et al., "Highly Enantioselective Synthesis of Cyclic and Funtionalized α-Amino Acids by Means of a Chiral Phase Transfer Catalyst", Tetrahedron Letters, 39:5347-5350 (1998).

Couché et al., "The Synthesis of Highly Functionalized Enantiometrically Enriched Cyclohexanes. An Approach to Carba-Sugars and Aminocarba-Sugars", Synlett, No. 1:87-89 (1999).

Daly and Poche, "The Preparation of N-Carboxyanhydrides of α-Amino Acids Using Bis(Trichloromethyl)Carbonate", Tetrahedron Letters 29(46):5859-5862 (1988).

Database CAPLUS on STN (Columbus OH, USA), Accession No. 4777908 Preparative Kinetic Resolution of 1-methylindene, Reaction in a Frozen System, Meurling, L. 1974.

Evans et al., "C$_2$—Symmetric Cu(II) Complexes as Chiral Lewis Acids. Catalytic Enantioselective Michael Addition of silylketene Acetals to Alkylidene Malonates", J. Am. Chem. Soc., 121:1994-1995 (1999).

Fang et al., "Catalytic Approach for the Formation of Optically Active Allyl α-Amino Acids by Addition of Allyl Metal Compounds to α-Imino Esters", J. Org. Chem., 64:4844-4849 (1999).

Ferraris et al., "Catalytic, Enatioselective Alkylation of α-Imino Esters Using Late Transition Metal Phosphine Complexes as Catalysts", J. Am. Chem. Soc., 120:4548-4549 (1998).

Fuller et al., "Urethane-Protected α-Amino Acid N-Carboxyanhydrides and Peptide Synthesis", Biopolymers (Peptide Science), 40:183-205 (1996).

Gottwald and Seebach,"Ring Opening With Kinetic Resolution of Azlactones by Ti-TADDOlates", Tetrahedron 55:723-738 (1999).

Grant and Grant, "Grant & Hackh's Chemical Dictionary", 5th Edition, McGraw-Hill, New York, pp. 558-559 (1990).

Grieco et al., "Fluoroprostaglandins: Total Synthesis of (+)-13-Fluoroprostaglandin F2 Methyl Ester", J. Org. Che., 50:3111-3115 (1985).

Hawley, Gessner, "The Condensed Chemical Dictionary", Van Nostrand, New York, pp. 823 (1997).

Heathcock et al. "Total Synthesis and Biological Evaluation of Structural Analogues of Compactin and Dihydromevinolin", J. Med. Chem. 30:1858-1873 (1987).

Hecker and Heathcock, "Total Synthesis of (+)- Dihydromevinolin", J. Am. Chem. Soc. 108:4586-4594 (1986).

Hiratake et al., "Catalytic Asymmetric Induction from ProchirainCyclic Acid Anydrides Using Cinchona Alkaloids", J. Chem. Soc. , Chem. Commun. pp. 1717-1719 (1985).

Hiratake et al., "Enantiotopic-Group Differentiation. Catalytic Asymmetric Ring-Opening of Prochiral Cyclic Acid Anydrides with Methanol, Using Cinchona Alkaloids", J. Chem. Soc. Perkin Trans. 1:1053-1058 (1987).

Huerta et al., "Dynamic Kinetic Resolution of α-Hydroxy Acid Esters", Organic Letters 2(8):1037-1040 (2000).

Ishitani et al., "Catalytic Enantioselective Synthesis of α-Aminonitriles with a Novel Zirconium Catalyst", Angew. Chem. Int. ed. 37(22):3186-3188 (1998).

Jaeschke and Seebach, "Highly Enantioselective Ring Opening of Cyclic Meso-Anydrides to Isopropyl Hemiesters with Ti-TADDOlates: An Alternative to Hydrolytic Enzymes?", J. Org. Chem., 63:1190-1197 (1998).

Kitamura et al., "Homogeneous Asymmetric Hydrogenetion of Funtionalized Ketones", J. Am. Chem. Soc., 110:629-631 (1988).

Kolasa and Miller, "Synthesis of Functionalized β-Lactams From Tartaric Acid", Tetrahedron, 45(10):3071-3080 (1989).

Konoike and Araki, "Practical Synthesis of Chiral Synthons for the Preparation of HMG-CoA Reductase Inhibitors", J. Org. Chem., 59:7849-7854 (1994).

Krueger et al., "Ti-Catalyzed Enantioselective Addition of Cyanide to Imines. A Practical Synthesis of Optically Pure α-Amino Acids", J. Am. Chem. Soc., 121:4284-4285 (1999).

Lee and Downie, "Sugar Esthers- IV- The Preparation of Chloroesters Under Essentially—Neutral Conditions", Tetrahedron 23:359-363 (1967).

Liang et al., "Dynamic Kinetic Resolutions Catalyzed by a Planar-Chiral Derivative of DMAP: Enantioselective Synthesis of Protected α-Amino Acids from Racemic Azlactones", J. Org. Chem., 63:3154-3155 (1998).

Mashima et al., "Cationic BINAP-RU (II) Halide Complexes: Highly Efficient Catalysts for Steroselective Asymmetric Hydrogenetion of α- and β- Functionalized Ketones", J. Org. Chem., 59:3064-3076 (1994).

Mori et al., "Synthesis of Optically Active Forms of Ipsdienol and Ipsenol", Tetrahedron 35:933-940 (1979).

O'Donnell et al., "An Efficient Homogeneous Catalytic Enantioselective Synthesis of α-Amino Acid Derivatives", Tetrahedron Letters, 39:8775-8778 (1998).

Ohtani et al., "Enantioselective Synthesis of S-1452, an Orally Active Potent Thromboxane $A_2$ Receptor Antagonist", J. Org. Chem., 56:2122-2127 (1991).

Ohtani et al., "Highly Effective and Practical Enantioselective Synthesis of Half-Esters of Bicyclo[2.2.1]heptanedicarboxylic Acid", J. Org. Chem., 56:4120-4123 (1991).

Ooi et al., "Molecular Design of $C_2$- Symmetric Chiral Phase-Transfer Catalyst for Practical Asymmetric Synthesis of α-Amino Acids", J. Am. Chem. Soc., 121:6519-6520 (1999).

Ooi et al., "Practical Catalytic Enantioselective Synthesis of α, α-Dialkyl-α-amino Acids by Chiral Phase-Transfer Catalysis", J. Am. Chem. Soc., 122:5228-5229 (2000).

Ozegowski et al., "The Different Behaviour of syn-and anti-2,3 Dimethylbutanedioic Anhydride in the Lipase-Catalyzed Enantioselective Alcoholysis", Tetrahedron Asymmetry 6(5):1191-1194 (1995).

Paterson et al., "Studies in Marine Macrolide Synthesis: Stereocontrolled Synthesis of the $C_1$-$C_{11}$ and $C_{15}$-$C_{27}$ Subunits of Aplyronine A", Tetrahedron Letters, 39:6037-6040 (1998).

Porter et al., "Ti-Catalyzed Regio- and Enantioselective Synthesis of Unsaturated α-Amino Nitriles, Amides and Acids, Catalyst Identification Through Screening of Parallel Libraries", J. Am. Chem. Soc., 122:2657-2658 (2000).

Roberts, J. D. and Caserio, M. C., "Basic Principles of Organic Chemistry", Benjamin, New York 288-289 (1964).

Romoff et al., "Urethane-Protected N-carboxyanhydrides (UNCAs) as Unique Reactants for the Study of Intrinsic Racemization Tendencies in Peptide Synthesis", Journal of Peptide Research, 49(4):281-292 (1997).

Rosen and Heathcock, "Total Synthesis of (+)-Compactin", J. Am. Chem., 107:3731-3733 (1985).

Seebach et al., "Highly Enantioselective Opening of Cyclic meso-Anhydrides to Isopropyl Hemiesters With Diisopropoxytitanium TADDOLates", Angew. Chem. Int. Ed. Engl., 34(21):2395-2396 (1995).

Seebach et al., "Resolution of Racemic Carboxylic Acid derivatives by TI-TADDOLate Mediated Esterification Reactions—A General Method for the Preparation of Enantiopure Compounds", Tetrahedron, 53(22):7539-7556 (1997).

Shimizu et al., "Enantioselective Esterification of Cyclic Discarboxylic Anhydrides Using Chiral Aminol Alcohols as Auxiliaries", Bull. Chem. Soc. Jpn, 66(7):2128-2130 (1993).

Sigman and Jacobsen, "Enantioselective Addition of Hydrogen Cyanide to Imines Catalyzed by a Chiral (Salen) Al (III) Complex", J. Am. Chem. Soc., 120:5315-5316 (1998).

Sigman and Jacobsen, "Schiff Base Catalysts for the Asymmetric Strecker Reaction Identified and Optimized from Parallel Synthetic Libraries", J. Am Chem. Soc., 120: 4901-4902 (1998).

Suzuki et al., "A Simple Synthesis of Bicyclo [2.2.1] Heptane System, A Key Potential Intermediate for Stable Prostaglandin $H_2$ Analogue", Heterocycles, 14(11):1735-1738 (1980).

Theisen et al., "Prochiral Recognition in the Reaction of 3- Substituted Glutaric Anhydrides with Chiral Secondary Alcohols", J. Org. Chem., 58:142-146 (1993).

Toyooka et al., "A Novel and Facile Synthesis of 5-Substituted 1,3-Dioxolane-2,4- Diones Using Trichloromethyl Chloroformate", Heterocycle, 29(5):975-978 (1989).

Toyota et al., "First Total Synthesis of (±)-Methyl Gummiferolate Using a Homoallyl- Homoallyl Radical Rearrangement Reaction", 1(10):1627-1629 (1999).

Wang et al., "Enantioselective Synthesis of α-Oxocarboxylic Acids to Enantiomerically Enriched α-Hydroxy Carboxylic Acids via Neighboring Group Control", Tetrahedron Letters, 39:5501-5504 (1998).

Wender et al., "Synthetic Studies on Arene-Olefin Cycloadditions. 11. Total Synthesis of (—)-Retigeranic Acid", Tetrahedron Letters, 31(18):2517-2520 (1990).

Yamamoto et al., "Asymmetric Synthesis of Optically Active Lactones from Cyclic Acid Anhydrides Using Lipase in Organic Solvents", Agric. Biol. Chem., 52(12):3087-3092 (1988).

Yamamoto et al., "Asymmetric Ring Opening of Cyclic Acid Anhydrides With Lipase in Organic Solvents", Tetrahedron Letters, pp. 1717-1720 (1988).

Hutzler, J.M. et al., "Inhibition of Cytochrome P450 2D6: Structure—Activity Studies Using a Series of Quinidine and Quinine Analogues," Chem. Res. Toxicol., 16(4):450-459 (2003).

Hiemstra, H. et al., "Addition of Aromatic Thiols to Conjugated Cycloalkenones, Catalyzed by Chiral β-Hydroxy Amines. A Mechanistic Study on Homogeneous Catalytic Asymmetric Synthesis," J. Am. Chem. Soc., 103(2):417-430 (1981).

Sharpless, K.B. et al., "New Ligands Double the Scope of the Catalytic Asymmetric Dihydroxylation of Olefins," The J. of Organic Chem., 56(15):4585-4588 (1991).

Supplementary Partial European Search Report for EP 04 75 5066 dated Jun. 12, 2007.

International Search Report for PCT/US04/18690 dated Oct. 30, 2006.

* cited by examiner

Figure 1

| Table1. Comparison of Catalysts' efficiency for methanolysis of 2,3-dimethylsuccinic anhydride in Et₂O at 0.02M concentration |||||||||||||
|---|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 |  | 0.1 | 0.02M | (DHQD)₂AQN | 5% | MeOH | 10eq | Et₂O | RT | 13h | 86 | 92% |
| 2 |  | 0.05 | 0.02M | QD-PP | 20% | MeOH | 10eq | Et₂O | RT | 48h | 93 | 87% |
| 3 |  | 0.1 | 0.02M | QD-TB | 20% | MeOH | 10eq | Et₂O | RT | 49h | 95 | 88% |
| 4 |  | 0.05 | 0.02M | QD-IP | 20% | MeOH | 10eq | Et₂O | RT | 25h | 99 | 86% |
| 5 |  | 0.05 | 0.02M | QD-PC | 20% | MeOH | 10eq | Et₂O | RT | 27.5h | 92 | 86% |
| 6 |  | 0.05 | 0.02M | QD-AD | 20% | MeOH | 10eq | Et₂O | RT | 2.5h/25h | 81/99 | 90% |
| 7 |  | 0.05 | 0.02M | QD-(-)-MN | 20% | MeOH | 10eq | Et₂O | RT | 7h | 99 | 89% |
| 8 |  | 0.05 | 0.02M | QD-(+)-MN | 20% | MeOH | 10eq | Et₂O | 19 | 9h | 96 | 89% |
| 9 |  | 0.05 | 0.02M | QD-AC | 20% | MeOH | 10eq | Et₂O | RT | 17h | 98 | 82% |
| 10 |  | 0.05 | 0.02M | QD-PIV | 20% | MeOH | 10eq | Et₂O | RT | 37d | 98 | 54% |
| 11 |  | 0.05 | 0.02M | QD-PH | 20% | MeOH | 10eq | Et₂O | RT | 75h | 97 | 85% |

Figure 2

| 12 | [structure] | 0.05 | 0.02M | QD-AN | 20% | MeOH | 10eq | Et₂O | RT | 25h | 90 | 86% |
| 13 | [structure] | 0.05 | 0.02M | QD-NT | 20% | MeOH | 10eq | Et₂O | RT | 48h | 94 | 78% |
| 14 | [structure] | 0.05 | 0.02M | QD-CN | 20% | MeOH | 10eq | Et₂O | RT | 258h | 96 | 81% |
| 15 | [structure] | 0.05 | 0.02M | Quinidine | 20% | MeOH | 10eq | Et₂O | RT | 2.5h | 94 | 70% |
| 16 | [structure] | 0.05 | 0.02M | Quinidine | 110% | MeOH | 10eq | Et₂O | RT | 2.5h | 100 | 74% |
| 17 | [structure] | 0.05 | 0.02M | QD-(+)-EF | 20% | MeOH | 10eq | Et₂O | RT | 14.5h | 99 | 88.5% |
| 18 | [structure] | 0.05 | 0.02M | QD-IB | 20% | MeOH | 10eq | Et₂O | RT | 16h | 96 | 87.5% |
| 19 | [structure] | 0.05 | 0.02M | QD-CH | 20% | MeOH | 10eq | Et₂O | RT | 13h | 97.7 | 88.5% |

Figure 3

Table 2. Comparison of Catalysts' efficiency for Triflouroethanolysis of 2,3-dimethylsuccinic anhydride in $Et_2O$ at 0.02M concentration

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield[a]) | ee % |
|---|---|---|---|---|---|---|---|---|---|---|---|---|
| 1 |  | 0.1 | 0.02M | (DHQD)₂AQN | 5% | CF₃CH₂OH | 10eq | Et₂O | RT | 53h | 100 | 87% |
| 2 |  | 0.1 | 0.02M | QD-PP | 20% | CF₃CH₂OH | 10eq | Et₂O | RT | 53h | 100 | 89% |
| 3 |  | 0.1 | 0.02M | QD-TB | 20% | CF₃CH₂OH | 10eq | Et₂O | RT | 13h | 100 (94) | 92% |
| 4 |  | 0.1 | 0.02M | QD-IP | 20% | CF₃CH₂OH | 10eq | Et₂O | RT | 25h | 100 (98) | 90% |
| 5 |  | 0.1 | 0.02M | QD-PC | 20% | CF₃CH₂OH | 10eq | Et₂O | RT | 13h | 100 (81) | 91% |
| 6 |  | 0.1 | 0.02M | QD-AD | 20% | CF₃CH₂OH | 10eq | Et₂O | RT | 24h | 100 | 95% |
| 7 |  | 0.1 | 0.02M | QD-(-)-MN | 20% | CF₃CH₂OH | 10eq | Et₂O | RT | 26h | 100 (99) | 92% |
| 8 |  | 0.1 | 0.02M | QD-(+)-MN | 20% | CF₃CH₂OH | 10eq | Et₂O | 19 | 21h | 100 (76) | 94% | a. The Purity of Crude Product was larger than 98% (NMR)

Figure 4

| Table3. Reaction Conditions Optimization for Methanolysis of 3-Methylglutaric Anhydride in Et$_2$O at 0.02M Concentration | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | Me-⟨⟩ | 0.1 | 0.02M | QD-AD | 50% | MeOH | 10eq | Et$_2$O | -27 | 96h | 98.6% (94%[a]) | 82% |
| 2 | Me-⟨⟩ | 0.1 | 0.02M | QD-AD | 100% | MeOH | 10eq | Et$_2$O | -27 | 50h | 99% (91%[b]) | 82% |
| 3 | Me-⟨⟩ | 0.1 | 0.02M | QD-AD | 50% | MeOH | 10eq | Et$_2$O | -40 | 79h | 63.5% (46%[b]) | 88% |
| 4 | Me-⟨⟩ | 0.1 | 0.02M | QD-AD | 100% | MeOH | 10eq | Et$_2$O | -40 | 96h | 89.1% | 89% |
| 5 | Me-⟨⟩ | 0.1 | 0.02M | QD-PP | 100% | MeOH | 10eq | Et$_2$O | -40 | 84.5h | 41% | 84% |
| 6 | Me-⟨⟩ | 0.1 | 0.02M | Quinidine | 110% | MeOH | 10eq | Et$_2$O | -40 | 84.5h | 26% (25%[b]) | 34% | a. The Purity of Crude Product was larger than 98% (by NMR)
b. Isolated yield with purity larger than 98% (by NMR)

Figure 5

Table 4. Screening of Reaction Conditions for Alcoholysis of 3-methyl-glutaric anhydride at 0.2M concentration

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
|---|---|---|---|---|---|---|---|---|---|---|---|---|
| 1 | Me-anhydride | 0.1 | 0.2M | QD-AD | 100% | $CF_3CH_2OH$ | 10eq | $Et_2O$ | -43 | 37.5h | 99% (95%[a]) | 70% |
| 2 | Me-anhydride | 0.1 | 0.2M | QD-AD | 100% | $CF_3CH_2OH$ | 1.5eq | $Et_2O$ | -43 | 72h | 93% | 88% |
| 3 | Me-anhydride | 0.1 | 0.2M | QD-AD | 100% | $CF_3CH_2OH$ | 10eq | Toluene | -43 | 19h | 99% (87%[a]) | 16% |
| 4 | Me-anhydride | 0.1 | 0.2M | QD-AD | 100% | $CF_3CH_2OH$ | 1.5eq | Toluene | -43 | 36.5h | 97% | 87% |
| 5 | Me-anhydride | 0.1 | 0.2M | QD-AD | 110% | MeOH | 1.5eq | $Et_2O$ | -53 | 141h | 86% (58%[b]) | 90% |
| 6 | Me-anhydride | 0.1 | 0.2M | QD-AD | 110% | MeOH | 1.5eq | Toluene | -53 | 86h | 98.4% (93%[b]) | 87% |
| 7 | Me-anhydride | 0.1 | 0.2M | QD-AD | 110% | $CF_3CH_2OH$ | 1.5eq | $Et_2O$ | -53 | 94h | 87.6% (70%[b]) | 90% |
| 8 | Me-anhydride | 0.1 | 0.2M | QD-AD | 110% | $CF_3CH_2OH$ | 1.5eq | Toluene | -53 | 49.5h | 98.5% (91%[b]) | 88% | a. The Purity of Crude Product was larger than 98% (by NMR)
b. Isolated yield with purity larger than 98% (by NMR)

Table5. Comparison of Catalysts' Efficiency for Methanolysis of 3-Methyl Glutaric Anhydride in Toluene at 0.2M Concentration

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
|---|---|---|---|---|---|---|---|---|---|---|---|---|
| 1 | Me-anhydride | 0.1 | 0.2 | QD-AD | 110% | MeOH | 1.5eq | Toluene | -43 | 40h | 90% | 86% |
| 2 | Me-anhydride | 0.1 | 0.2 | QD-(-)-MN | 110% | MeOH | 1.5eq | Toluene | -43 | 42h | 91.5% | 85% |
| 3 | Me-anhydride | 0.1 | 0.2 | QD-PP | 110% | MeOH | 1.5eq | Toluene | -43 | 77.5h | 92% (69%[a]) | 77% |
| 4 | Me-anhydride | 0.1 | 0.2 | (DHQD)$_2$AQN | 55% | MeOH | 1.5eq | Toluene | -43 | 17h | 96.2% | 88% | a. Isolated yield with purity larger than 98% (by NMR)

Figure 6

| Table 6. Comparison of Catalysts' Efficiency for Triflouroethanolysis of 3-Methyl Glutaric Anhydride in Toluene at 0.2M Concentration | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | Me-anhydride | 0.1 | 0.2 | QD-AD | 110% | $CF_3CH_2OH$ | 1.5eq | Toluene | -43 | 23.5h | 98.2%(88%[a]) | 86% |
| 2 | Me-anhydride | 0.1 | 0.2 | QD-(-)-MN | 110% | $CF_3CH_2OH$ | 1.5eq | Toluene | -43 | 23.5h | 94.7% | 88% |
| 3 | Me-anhydride | 0.1 | 0.2 | QD-PP | 110% | $CF_3CH_2OH$ | 1.5eq | Toluene | -43 | 70.5h | 93% (65%[b]) | 77% |
| 4 | Me-anhydride | 0.1 | 0.2 | (DHQD)$_2$AQN | 55% | $CF_3CH_2OH$ | 1.5eq | Toluene | -43 | 44h | 97.5% | 74% | a. The Purity of Crude Product was larger than 98% (by NMR)
b. Isolated yield with purity larger than 98% (by NMR)

Figure 7

| Table7. Comparison of Catalysts' Efficiency for Methanolysis of 3-Phenyl Glutaric Anhydride in Toluene at 0.2M Concentration |||||||||||||
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | Ph- structure | 0.1 | 0.2 | QD-AD | 110% | MeOH | 1.5eq | Toluene | -43 | 24.5h | 98.7% (92%[a]) | 86% |
| 2 | Ph- structure | 0.1 | 0.2 | QD-(-)-MN | 110% | MeOH | 1.5eq | Toluene | -43 | 29h | 100%(100%[a]) | 84% |
| 3 | Ph- structure | 0.1 | 0.2 | QD-PP | 110% | MeOH | 1.5eq | Toluene | -43 | 52h | 91.5% (73%[b]) | 79% |
| 4 | Ph- structure | 0.1 | 0.2 | (DHQD)$_2$AQN | 55% | MeOH | 1.5eq | Toluene | -43 | 18h | 100% (98%[a]) | 90% | a. The Purity of Crude Product was larger than 98% (by NMR)
b. Isolated yield with purity larger than 98% (by NMR)

Figure 8

Table 8. Comparison of Catalysts' Efficiency for Triflouroethanolysis of 3-Phenyl Glutaric Anhydride in Toluene at 0.2M Concentration

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
|---|---|---|---|---|---|---|---|---|---|---|---|---|
| 1 | Ph-[anhydride] | 0.1 | 0.2 | QD-AD | 110% | CF₃CH₂OH | 1.5eq | Toluene | -43 | 35.5h | 100% (91%ᵃ) | 91% |
| 2 | Ph-[anhydride] | 0.1 | 0.2 | QD-(-)-MN | 110% | CF₃CH₂OH | 1.5eq | Toluene | -43 | 23.5h | 97.7% | 90% |
| 3 | Ph-[anhydride] | 0.1 | 0.2 | QD-PP | 110% | CF₃CH₂OH | 1.5eq | Toluene | -43 | 71.5h | 97% | 81% |
| 4 | Ph-[anhydride] | 0.1 | 0.2 | (DHQD)₂AQN | 55% | CF₃CH₂OH | 1.5eq | Toluene | -43 | 44.5h | 100% (84%ᵃ) | 81% | a. The Purity of Crude Product was larger than 98% (by NMR)

Figure 9

Table 9  Comparison of Catalysts' Efficiency for Methanolysis of 3-Isopropyl Glutaric Anhydride in Toluene at 0.2M Concentration

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
|---|---|---|---|---|---|---|---|---|---|---|---|---|
| 1 | | 0.1 | 0.2 | QD-AD | 110% | MeOH | 1.5eq | Toluene | -43 | 36.5h | 96% | 87% |
| 2 | | 0.1 | 0.2 | QD-(-)-MN | 110% | MeOH | 1.5eq | Toluene | -43 | 42h | 97% | 86% |
| 3 | | 0.1 | 0.2 | QD-PP | 110% | MeOH | 1.5eq | Toluene | -43 | 91h | 90.3% | 80% |
| 4 | | 0.1 | 0.2 | (DHQD)$_2$AQN | 55% | MeOH | 1.5eq | Toluene | -43 | 36.5h | 99% (86%[a]) | 88% | a. The Purity of Crude Product was larger than 98% (by NMR)

Figure 10

| Table10. Comparison of Catalysts' Efficiency for Triflouroethanolysis of 3-Isopropyl Glutaric Anhydride in Toluene at 0.2M Concentration ||||||||||||
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | | 0.1 | 0.2 | QD-AD | 110% | CF$_3$CH$_2$OH | 1.5eq | Toluene | -43 | 52h | 98.2% (87%[a]) | 89% |
| 2 | | 0.1 | 0.2 | QD-(-)-MN | 110% | CF$_3$CH$_2$OH | 1.5eq | Toluene | -43 | 61h | 96.4% | 87% |
| 3 | | 0.1 | 0.2 | QD-PP | 110% | CF$_3$CH$_2$OH | 1.5eq | Toluene | -43 | 91h | 90.9% | 55% |
| 4 | | 0.1 | 0.2 | (DHQD)$_2$AQN | 55% | CF$_3$CH$_2$OH | 1.5eq | Toluene | -43 | 51h | 96.7% | 78% | a. The Purity of Crude Product was larger than 98% (by NMR)

| Table 11 Comparison of Catalysts' Efficiency for Methanolysis of 3-TBSO Glutaric Anhydride in Toluene at 0.2M Concentration ||||||||||||
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | TBSO | 0.1 | 0.2 | QD-AD | 110% | MeOH | 1.5eq | Toluene | -43 | 56h | 95.7% | 92% |
| 2 | TBSO | 0.1 | 0.2 | QD-(-)-MN | 110% | MeOH | 1.5eq | Toluene | -43 | 42h | 94% | 92% |
| 3 | TBSO | 0.1 | 0.2 | QD-PP | 110% | MeOH | 1.5eq | Toluene | -43 | 105h | 91.5% | 78% |
| 4 | TBSO | 0.1 | 0.2 | (DHQD)$_2$AQN | 55% | MeOH | 1.5eq | Toluene | -43 | 33.5h | 97.2% | 95% |

Figure 13

| Table12. Comparison of Catalysts' Efficiency for Triflouroethanolysis of 3-TBSO Glutaric Anhydride in Toluene at 0.2M Concentration | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | TBSO | 0.1 | 0.2 | QD-AD | 110% | $CF_3CH_2OH$ | 1.5eq | Toluene | -43 | 71h | 97.8% | 85% |
| 2 | TBSO | 0.1 | 0.2 | QD-(-)-MN | 110% | $CF_3CH_2OH$ | 1.5eq | Toluene | -43 | 91h | 97.1% | 89% |
| 3 | TBSO | 0.1 | 0.2 | QD-PP | 110% | $CF_3CH_2OH$ | 1.5eq | Toluene | -43 | 105h | 87% (68%[a]) | 48% |
| 4 | TBSO | 0.1 | 0.2 | (DHQD)$_2$AQN | 55% | $CF_3CH_2OH$ | 1.5eq | Toluene | -43 | 81h | 94.2% | 79% | a. Isolated yield with purity larger than 98% (by NMR)

| Table 13 Q-AD Catalyzed Methanolysis of 3-Substitutedglutaric Anhydride in Toluene at 0.2M Concentration ||||||||||||
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. ($^{\circ}$C) | Reaction Time | Conversion % (%Yield) | ee % |
| 1 | Me- | 0.1 | 0.2 | Q-AD | 110% | MeOH | 1.5eq | Toluene | -43 | 88h | 80.4% (64%[a]) | 69% |
| 2 | Ph- | 0.1 | 0.2 | Q-AD | 110% | MeOH | 1.5eq | Toluene | -43 | 78h | 97% | 68% |
| 3 | iPr- | 0.1 | 0.2 | Q-AD | 110% | MeOH | 1.5eq | Toluene | -43 | 88h | 86% | 78% |
| 4 | TBSO- | 0.1 | 0.2 | Q-AD | 110% | MeOH | 1.5eq | Toluene | -43 | 105h | 87% | 75% | a. Isolated yield with purity larger than 98% (NMR)

Figure 14

| Table14 Q-AD Catalyzed Triflouroethanolysis of 3-Substitutedglutaric anhydride in Toluene at 0.2M concentration |||||||||||||
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | Me- | 0.1 | 0.2 | Q-AD | 110% | CF$_3$CH$_2$OH | 1.5eq | Toluene | -43 | 88h | 96% | 76% |
| 2 | Ph- | 0.1 | 0.2 | Q-AD | 110% | CF$_3$CH$_2$OH | 1.5eq | Toluene | -43 | 78h | 98.1% (96%[a]) | 80% |
| 3 | | 0.1 | 0.2 | Q-AD | 110% | CF$_3$CH$_2$OH | 1.5eq | Toluene | -43 | 68h | 89% | 80% |
| 4 | TBSO- | 0.1 | 0.2 | Q-AD | 110% | CF$_3$CH$_2$OH | 1.5eq | Toluene | -43 | 105h | 88% | 69% | a. The Purity of Crude Product was larger than 98% (by NMR)

Figure 15

| Table 15. Comparison of Catalysts' Efficiency for the Alcoholysis of cis-1, 2, 3, 6-Tetrahydrophthalic Anhydride with Methanol in Et₂O at 0.02M concentration. | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % | ee % |
| 1 |  | 0.1 | 0.02M | QD-AD | 20% | MeOH | 10eq | Et₂O | r.t. | 2 h | 100% | 92% |
| 2 |  | 0.1 | 0.02M | QD-AD | 20% | MeOH | 10eq | Et₂O | -25 | 48 h | 100% | 96% |
| 3 |  | 0.1 | 0.02M | (DHQD)2AQN | 7% | MeOH | 10eq | Et₂O | -20 | 60 h | 100 | 98% |

Table 16. Comparison of Catalysts' Efficiency for the Alcoholysis of cis-1, 2, 3, 6-Tetrahydrophthalic Anhydride with Trifluoroethanol in Et₂O at 0.02M concentration.

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % | ee % |
|---|---|---|---|---|---|---|---|---|---|---|---|---|
| 1 |  | 0.1 | 0.02M | QD-AD | 20% | CF₃CH₂OH | 10eq | Et₂O | r.t. | 4 h | 100% | 94% |
| 2 |  | 0.1 | 0.02M | QD-AD | 20% | CF₃CH₂OH | 10eq | Et₂O | -25 | 18 h | 100% | 98% |
| 3 |  | 0.1 | 0.02M | (DHQD)₂AQN | 10% | CF₃CH₂OH | 10eq | Et₂O | r.t. | 2 h | 100% | 94% |
| 4 |  | 0.1 | 0.02M | (DHQD)₂AQN | 10% | CF₃CH₂OH | 10eq | Et₂O | -25 | 48 h | 100% | 96% |
| 5 |  | 0.1 | 0.02M | QD-PP | 20% | CF₃CH₂OH | 10eq | Et₂O | r.t. | 2 h | 100% | 90% |
| 6 |  | 0.1 | 0.02M | QD-PP | 20% | CF₃CH₂OH | 10eq | Et₂O | -25 | 48 h | 100% | 94% |
| 7 |  | 0.1 | 0.02M | QD-MN | 20% | CF₃CH₂OH | 10eq | Et₂O | -27 | 24 h | 100 | 96% |
| 8 |  | 0.1 | 0.02M | QD-PP | 100% | CF₃CH₂OH | 10eq | Et₂O | -27 | 12 h | 100 | 87% |

Figure 18

Table 17. QD-AD-Catalyzed Alcoholysis of 1,2-Cyclohexanedicarboxylic Anhydride with Methanol in Et₂O at 0.02M concentration.

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % | ee % |
|---|---|---|---|---|---|---|---|---|---|---|---|---|
| 1 |  | 0.1 | 0.02M | QD-AD | 20% | MeOH | 10eq | Et₂O | r.t. | 4h | 100 | 91% |
| 2 |  | 0.1 | 0.02M | QD-AD | 50% | MeOH | 10eq | Et₂O | r.t. | 4h | 100 | 91% |
| 3 |  | 0.1 | 0.02M | QD-AD | 100% | MeOH | 10eq | Et₂O | r.t. | 4h | 100 | 91% |
| 4 |  | 0.1 | 0.02M | QD-AD | 20% | MeOH | 10eq | Et₂O | -25 | 37h | 100 | 92% |
| 5 |  | 0.1 | 0.02M | QD-AD | 50% | MeOH | 10eq | Et₂O | -25 | 37h | 100 | 94% |
| 6 |  | 0.1 | 0.02M | QD-AD | 100% | MeOH | 10eq | Et₂O | -25 | 37h | 100 | 91% |

Figure 19

| Table 18. Comparison of Catalysts' Efficiency for the Alcoholysis of 1,2-Cyclohexanedicarboxylic Anhydride with Trifluoroethanol in Et₂O at 0.02M concentration. | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % | ee % |
| 1 | | 0.1 | 0.02M | QD-AD | 20% | CF₃CH₂OH | 10eq | Et₂O | r.t. | 2h | 100 | 94% |
| 2 | | 0.1 | 0.02M | QD-PP | 20% | CF₃CH₂OH | 10eq | Et₂O | r.t. | 5h | 100 | 89% |
| 3 | | 0.1 | 0.02M | (DHQD)₂AQN | 10% | CF₃CH₂OH | 10eq | Et₂O | r.t. | 2h | 100 | 90% |
| 4 | | 0.1 | 0.02M | QD-AD | 20 | CF₃CH₂OH | 10eq | Et₂O | -25 | 16h | 100 | 96% |
| 5 | | 0.1 | 0.02M | QD-PP | 20 | CF₃CH₂OH | 10eq | Et₂O | -25 | 16h | 100 | 91% |
| 6 | | 0.1 | 0.02M | (DHQD)₂AQN | 10 | CF₃CH₂OH | 10eq | Et₂O | -25 | 16h | 100 | 90% |
| 7 | | 0.1 | 0.02M | QD-MN | 20 | CF₃CH₂OH | 10eq | Et₂O | -25 | 24h | 100 | 95% |

Figure 20

| Table 19. Comparison of Catalysts' efficency for the alcoholysis of cis-5-norbornene-endo-2,3-dicarboxylic anhydride in Et₂O at 0.02M Concentration. | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 |  | 0.1 | 0.02M | QD-AD | 30 | MeOH | 10eq | Et₂O | -27 | 3d | 100(98) | 96% |
| 2 |  | 0.1 | 0.02M | QD-MN | 30 | MeOH | 10eq | Et₂O | -27 | 7d | 100(96) | 97% |
| 3 |  | 0.1 | 0.02M | (DHQD)₂AQN | 15 | MeOH | 10eq | Et₂O | -27 | 3d | 100(97) | 95% |
| 4 |  | 0.1 | 0.02M | QD-PP | 30 | MeOH | 10eq | Et₂O | -27 | 3d | 100(81) | 79% |
| 5 |  | 0.1 | 0.02M | QD-PP | 100 | MeOH | 10eq | Et₂O | -27 | 4.5d | 100(96) | 84% |

Figure 21

| Table 20. Comparison of Catalysts' Efficiency for the Alcoholysis of exo-3,6-epoxy-1,2,3,6-tetrahydrophthalic Anhydride in Et₂O at 0.02M. |||||||||||||
|---|---|---|---|---|---|---|---|---|---|---|---|---|
| Entry # | Substrate | Substrate Loading | Substrate Concentration | Catalyst | Catalyst (mol%) | Alcohol | Alcohol Loading | Solvent | Temp. (°C) | Reaction Time | Conversion % (%Yield) | ee % |
| 1 |  | 0.1 | 0.02M | QD-AD | 40% | MeOH | 10eq | Et₂O | -27 | 36 h | 100(97) | 98% |
| 2 |  | 0.1 | 0.02M | QD-MN | 40% | MeOH | 10eq | Et₂O | -27 | 3 d | 100(77) | 97% |
| 3 |  | 0.1 | 0.02M | QD-PP | 30% | MeOH | 10eq | Et₂O | -27 | 3 d | 100(78) | 85% |
| 4 |  | 0.1 | 0.02M | QD-PP | 100% | MeOH | 10eq | Et₂O | -27 | 36 h | 100(85) | 84% |
| 5 |  | 0.1 | 0.02M | (DHQD)2AQN | 20% | MeOH | 10eq | Et2O | -20 | 4d | 100(74) | 92% |

| Table 21. Reaction Conditions Optimization for the Alcoholysis of cis-1,2,3,6-Tetrahydrophthalic Anhydride in Et₂O at 0.2M | | | | | | | | | | | |
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % | ee % |
| 1 | | 0.1 | 0.2M | QD-AD | 20% | CF₃CH₂OH | 10 | Et₂O | -25 | 12 h | 100 | 92% |
| 2 | | 0.1 | 0.2M | QD-MN | 20% | CF₃CH₂OH | 10 | Et₂O | -25 | 12 h | 100 | 92% |
| 3 | | 0.1 | 0.2M | QD-AD | 100% | CF₃CH₂OH | 10 | Et₂O | -25 | 4 h | 100 | 98% |
| 4 | | 0.1 | 0.2M | QD-MN | 100% | CF₃CH₂OH | 10 | Et₂O | -25 | 4 h | 100 | 98% |
| 5 | | 0.1 | 0.2M | QD-AD | 100% | CF₃CH₂OH | 1.5 | Et₂O | -25 | 3 d | 100 | 98% |
| 6 | | 0.1 | 0.2M | QD-MN | 100% | CF₃CH₂OH | 1.5 | Et₂O | -25 | 3 d | 100 | 99% |

Table 22. Reaction Conditions Optimization for the Alcoholysis of cis-1,2,3,6-Tetrahydrophthalic Anhydride in Toluene at 0.2M

| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
|---|---|---|---|---|---|---|---|---|---|---|---|---|
| 1 |  | 0.1 | 0.2M | QD-AD | 20% | CF$_3$CH$_2$OH | 10 | toluene | -25 | 12 h | 100 | 51% |
| 2 |  | 0.1 | 0.2M | QD-MN | 20% | CF$_3$CH$_2$OH | 10 | toluene | -25 | 12 h | 100 | 48% |
| 3 |  | 0.1 | 0.2M | QD-AD | 100% | CF$_3$CH$_2$OH | 10 | toluene | -25 | 4 h | 100 | 80% |
| 4 |  | 0.1 | 0.2M | QD-MN | 100% | CF$_3$CH$_2$OH | 10 | toluene | -25 | 4 h | 100 | 76% |
| 5 |  | 0.1 | 0.2M | QD-AD | 100% | CF$_3$CH$_2$OH | 1.5 | toluene | -25 | 3 d | 100(99) | >99% |
| 6 |  | 0.1 | 0.2M | QD-MN | 100% | CF$_3$CH$_2$OH | 1.5 | toluene | -25 | 3 d | 100(99) | 99% |

| Table 23. Reaction Conditions Optimization for the Alcoholysis of cis-1,2,3,6-Tetrahydrophthalic Anhydride in Toluene at 0.5M | | | | | | | | | | | | |
|---|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % | ee % |
| 1 | | 0.1 | 0.5M | QD-AD | 100% | $CF_3CH_2OH$ | 1.5 | toluene | -25 | 7 d | 94 | NA |
| 2[a] | | 0.1 | 0.5M | QD-MN | 110% | $CF_3CH_2OH$ | 1.5 | toluene | -25 | 3 d | 100 | >99% |

[a]With 4Å molecular sieves.

Figure 24

| Table 24. Alcoholysis of Succinic Anhydrides with Q-AD |||||||||||||
|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 |  | 0.1 mmol | 0.02 M | Q-AD | 20% | $CF_3CH_2OH$ | 10 equiv | Ether | -27 | 48 h | 100(91%) | 94% |
| 2 |  | 0.1 mmol | 0.02M | Q-AD | 20% | $CF_3CH_2OH$ | 10 equiv | Ether | -27 | 48 h | 100(99) | 90% |
| 3 |  | 0.1 mmol | 0.02M | Q-AD | 30% | $CH_3OH$ | 10 equiv | Ether | -27 | 5 days | 100(92) | 76% |
| 4 |  | 0.1 mmol | 0.02 M | Q-AD | 30% | $CH_3OH$ | 10 equiv | Ether | -27 | 3 days | 100(70) | 82% |

Figure 25

| Table 25. Comparison of Catalysts' efficiency for methanolysis of 2,3-dimethylsuccinic anhydride in Et₂O at 0.02M concentration ||||||||||||
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
|---|---|---|---|---|---|---|---|---|---|---|---|---|
| 1 |  | 0.05 | 0.02M | QD-AA | 20% | MeOH | 10eq | Et₂O | RT | 23.5h | 97.4 | 79.0% |
| 2 |  | 0.05 | 0.02M | QD-MP | 20% | MeOH | 10eq | Et₂O | RT | 19.5h | 98.6 | 87.0% |
Figure 26

| Table 26. Comparison of Catalysts' Efficiency for Triflouroethanolysis of 3-Isopropyl Glutaric Anhydride in Toluene at 0.2M Concentration |||||||||||||
|---|---|---|---|---|---|---|---|---|---|---|---|---|
| Entry # | Substrate | Substrate Loading (mmol) | Substrate Concentration | Catalyst | Catalyst Loading (mol%) | Alcohol | Alcohol Loading (eq.) | Solvent | Temp. (°C) | Reaction Time | Conversion % (%Yield) | ee % |
| 1 | | 0.13 | 0.2 | QD-CH | 110% | $CF_3CH_2OH$ | 1.5eq | Toluene | -43 | 107h | 97.2% | 76% |
| 2 | | 0.113 | 0.2 | QD-MP | 110% | $CF_3CH_2OH$ | 1.5eq | Toluene | -43 | 22h | 70.9% | 79% |

Figure 27

(DHQ)₂AQN  (DHQD)₂AQN

Figure 29
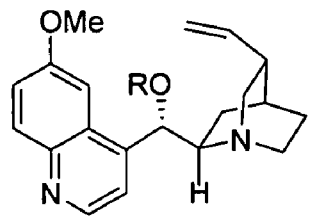
*quinidine-based catalysts*
| Catalyst | R |
|---|---|
| QD-PH |  |
| QD-AN | 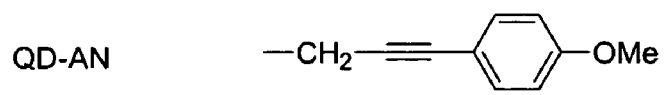 |
| QD-NT | 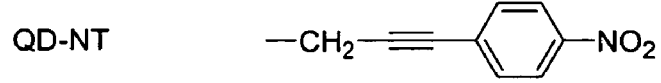 |
| QD-AC |  |
| QD-CH | 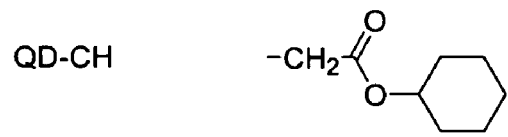 |

CINCHONA-ALKALOID-BASED CATALYSTS, AND ASYMMETRIC ALCOHOLYSIS OF CYCLIC ANHYDRIDES USING THEM

RELATED APPLICATIONS

This application claims the benefit of priority to U.S. Provisional Patent Application Ser. No. 60/477,531, filed Jun. 11, 2003; and U.S. Provisional Patent Application Ser. No. 60/484,218, filed Jul. 1, 2003.

GOVERNMENT SUPPORT

The invention described herein was supported in part by National Institutes of Health Grant Number NIH GM61591; therefore, the government has certain rights to this invention.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News*, Sep. 28, 1992, pp. 46-79) include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming.

One method of obtaining enantiomerically pure materials is by enantioselective alcoholysis of meso, prochiral, and racemic cyclic anhydrides (EACA). These reactions appear to be broadly applicable to both research and industrial scale a symmetric synthesis of a wide variety of important chiral building blocks, such as hemiester, α-amino acids and α-hydroxy acids. Commercially available modified dimeric cinchona alkaloids (DHQD)$_2$AQN, (DHQ)$_2$AQN, have been identified recently by Deng and coworkers as enantioselective and recyclable catalysts for enantioselective alcoholyses of cyclic anhydrides. However, commercially available (DHQD)$_2$AQN is expensive. For example, the commercial price (Aldrich Chemical Company) for a mole of (DHQD)$_2$AQN is more than $100,000.00. Furthermore, the dimeric catalyst is not available in large quantity (e.g., in kilogram quantity). Therefore, the stereoselective alcoholysis of cyclic anhydrides using dimeric catalysts is not practical on a relatively large scale (>0.1 mol). Consequently, the development of a new generation of monomeric catalysts that is comparably effective to (DHQD)$_2$AQN, but substantially less costly to produce, is of significant practical value. Remarkably, we have developed such monomeric catalysts for asymmetric alcoholysis of cyclic anhydrides.

SUMMARY OF THE INVENTION

One aspect of the present invention relates generally to cinchona-alkaloid-based catalysts. In certain embodiments, the quinidine-based catalyst contains a ketone, ester, amide, cyano, or alkynyl group. In preferred embodiments, the catalyst is QD-IP, QD-(−)-MN, or QD-AD. In other embodiments, the cinchona-alkaloid-based catalyst is Q-AD.

Another aspect of the invention relates to a method of preparing a derivatized cinchona alkaloid catalyst by reacting a cinchona-alkaloid with base and a compound that has a suitable leaving group. In certain embodiments, the leaving group is Cl, Br, I, OSO$_2$CH$_3$, or OSO$_2$CF$_3$. In a preferred embodiment, the leaving group is Cl. In a preferred embodiment, the base is a metal hydride. In a preferred embodiment, the hydroxyl group of the cinchona alkaloid undergoes reaction with an alkyl chloride to form the catalyst.

Another aspect of the present invention relates to a method of preparing a chiral, non-racemic compound from a prochiral cyclic anhydride or a meso cyclic anhydride, comprising the step of: reacting a prochiral cyclic anhydride or a meso cyclic anhydride with a nucleophile in the presence of a catalyst; wherein said prochiral cyclic anhydride or meso cyclic anhydride comprises an internal plane of symmetry or point of symmetry or both; thereby producing a chiral, non-racemic compound; wherein said catalyst is a derivatized cinchona-alkaloid. In preferred embodiments, the catalyst is QD-IP, QD-(−)-MN, or QD-AD. In certain embodiments, the nucleophile is a primary alcohol.

In a preferred embodiment, the nucleophile is methanol or CF$_3$CH$_2$OH. In certain embodiments, the prochiral cyclic anhydride or meso cyclic anhydride is a substituted succinic anhydride or a substituted glutaric anhydride. In certain embodiments, the catalyst is present in less than about 70 mol % relative to said prochiral cyclic anhydride or meso cyclic anhydride. In a preferred embodiment, the catalyst is present in less than about 10 mol % relative to said prochiral cyclic anhydride or meso cyclic anhydride. In certain embodiment, the chiral, non-racemic compound has an enantiomeric excess greater than about 90%. In certain, embodiments, said catalyst is Q-IP, Q-PC, Q-AD, or Q-(−)-MN.

Another aspect of the present invention relates to a method of kinetic resolution, comprising the step of: reacting a racemic cyclic anhydride with an alcohol in the presence of a derivatized cinchona-alkaloid catalyst. In preferred embodiments, the catalyst is QD-IP, QD-(−)-MN, or QD-AD. In a preferred embodiment, the alcohol is a primary alcohol. In certain embodiments, the catalyst is Q-IP, Q-PC, Q-AD, or Q-(−)-MN.

BRIEF DESCRIPTION OF THE DRAWINGS

FIG. 1 presents a comparison of catalysts' efficiency for methanolysis of 2,3-dimethylsuccinic anhydride in Et$_2$O at 0.02 M concentration.

FIG. 2 presents a comparison of catalysts' efficiency for methanolysis of 2,3-dimethylsuccinic anhydride in Et$_2$O at 0.02 M concentration.

FIG. 3 presents a comparison of catalysts' efficiency for trifluoroethanolysis of 2,3-dimethylsuccinic anhydride in Et$_2$O at 0.02 M concentration.

FIG. 4 presents reaction conditions optimization for methanolysis of 3-methylglutaric anhydride in Et$_2$O and 0.02 M concentration.

FIG. 5 presents screening of reaction conditions for alcoholysis of 3-methyl-glutaric anhydride at 0.2 M concentration.

FIG. 6 presents a comparison of catalysts' efficiency for methanolysis of 3-methyl glutaric anhydride in toluene at 0.2 M concentration.

FIG. 7 presents a comparison of catalysts' efficiency for trifluoroethanolysis of 3-methyl glutaric anhydride in toluene at 0.2 M concentration.

FIG. 8 presents a comparison of catalysts' efficiency for methanolysis of 3-phenyl glutaric anhydride in toluene at 0.2 M concentration.

FIG. 9 presents a comparison of catalysts' efficiency for trifluoroethanolysis of 3-phenyl glutaric anhydride in toluene at 0.2 M concentration.

FIG. 10 presents a comparison of catalysts' efficiency for methanolysis of 3-isopropyl glutaric anhydride in toluene at 0.2 M concentration.

FIG. 11 presents a comparison of catalysts' efficiency for trifluoroethanolysis of 3-isopropyl glutaric anhydride in toluene at 0.2 M concentration.

FIG. 12 presents a comparison of catalysts' efficiency for methanolysis of 3-TBSO glutaric anhydride in toluene at 0.2 M concentration.

FIG. 13 presents a comparison of catalysts' efficiency for trifluoroethanolysis of 3-TBSO glutaric anhydride in toluene at 0.2 M concentration.

FIG. 14 presents Q-AD catalyzed methanolysis of 3-substituted glutaric anhydride in toluene at 0.2 M concentration.

FIG. 15 presents Q-AD catalyzed trifluoromethanolysis of 3-substituted glutaric anhydride in toluene at 0.2 M concentration.

FIG. 16 presents a comparison of catalysts' efficiency for the alcoholysis of cis-1,2,3,6-tetrahydrophthalic anhydride with methanol in Et$_2$O at 0.02 M concentration.

FIG. 17 presents a comparison of catalysts' efficiency for the alcoholysis of cis-1,2,3,6-tetrahydrophthalic anhydride with trifluoroethanol in Et$_2$O at 0.02 M concentration.

FIG. 18 presents QD-AD catalyzed alcoholysis of 1,2-cyclohexanedicarboxylic anhydride with methanol in Et$_2$O at 0.02 M concentration.

FIG. 19 presents a comparison of catalysts' efficiency for the alcoholysis of 1,2-cyclohexanedicarboxylic anhydride with trifluoroethanol in Et$_2$O at 0.02 M concentration.

FIG. 20 presents a comparison of catalysts' efficiency for the alcoholysis of cis-norbornene-endo-2,3-dicarboxylic anhydride in Et$_2$O at 0.02 M concentration.

FIG. 21 presents a comparison of catalysts' efficiency for the alcoholysis of exo-3,6-epoxy-1,2,3,6-tetrahydrophthalic anhydride in Et$_2$O at 0.02 M concentration.

FIG. 22 presents reaction conditions optimization for the alcoholysis of cis-1,2,3,6-tetrahydrophthalic anhydride in Et$_2$O at 0.02 M.

FIG. 23 presents reaction conditions optimization for the alcoholysis of cis-1,2,3,6-tetrahydrophthalic anhydride in toluene at 0.2 M.

FIG. 24 presents reaction conditions optimization for the alcoholysis of cis-1,2,3,6-tetrahydrophthalic anhydride in toluene at 0.5 M.

FIG. 25 presents alcoholysis of succinic anhydrides with Q-AD.

FIG. 26 presents a comparison of catalysts' efficiency for methanolysis of 2,3-dimethylsuccinic anhydride in in Et$_2$O at 0.02 M concentration.

FIG. 27 presents a comparison of catalysts' efficiency for trifluoroethanolysis of 3-isopropyl glutaric anhydride in toluene at 0.2 M concentration.

FIG. 29 depicts the structures of QD-PH, QD-AN, QD-NT, QD-AC and QD-CH.

DETAILED DESCRIPTION OF THE INVENTION

Figure 28:
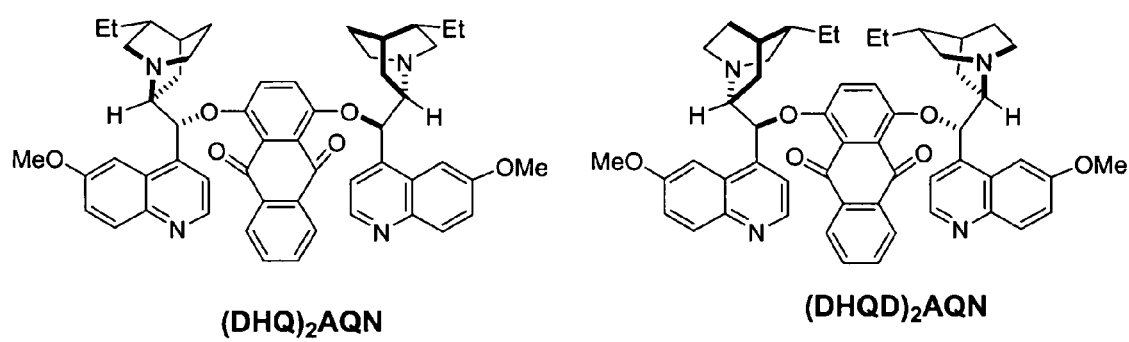
FIG. 28 depicts the structures of dimeric catalysts (DHQD)$_2$AQN and (DHQ)$_2$AQN.

The ability to transform selectively a prochiral or meso compound into an enantiomerically enriched or enantiomerically pure chiral compound has broad application, especially in the agricultural and pharmaceutical industries, as well as in the polymer industry. Enantioselective opening of the readily accessible prochiral or meso cyclic anhydrides generates enantiomerically enriched chiral hemiesters containing one or multiple stereogenic centers and two chemically differentiated carbonyl functionalities (eq. 1). These optically active bifunctional hemiesters are versatile chiral building blocks in asymmetric synthesis. See Toyota, M.; Yokota, M.; Ihara, M. *Organic Lett.* 1999, 1, 1627-1629; Ohtani, M.; Matsuura, T.; Watanabe, F.; Narisada, M. *J. Org. Chem.* 1991, 56, 4120-4123; and Suzuki, T.; Tomino, A.; Matsuda, Y.; Unno, K.; Kametani, T. *Heterocycles*, 1980, 14, 1735-1738.

Due to its great significance for organic synthesis, the development of method for the enantioselective desymmetrization of prochiral and meso cyclic anhydrides has been a topic of research. See Jaeschke, G.; Seebach, D. *J. Org. Chem.* 1998, 63, 1190-1197 and Yamamoto, K.; Nishioka, T.; Oada, J. *Tetrahedron Lett.* 1988, 29, 1717-1720. Synthetically useful selectivity has been obtained in desymmetrizations assisted by a stoichiometric amounts of chiral auxiliaries or chiral mediators. See Konoike, T.; Araki, Y. *J. Org. Chem.* 1994, 59, 7849-7854. Despite considerable efforts, the development of a general and effective catalytic desymmetrization of prochiral and meso cyclic anhydrides has not yet been achieved. See Hiratake, J.; Inagaki, M.; Yamamoto, Y.; Oada, J. *J. Chem. Soc. Perkin. Trans. I* 1987, 1053-1058.

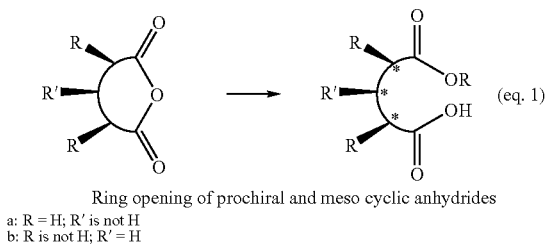

(eq. 1)

Ring opening of prochiral and meso cyclic anhydrides
a: R = H; R' is not H
b: R is not H; R' = H
c: R is not H; R' is not H Our general interests in asymmetric catalysis using chiral Lewis bases focused our attention on the amine-catalyzed alcoholysis of cyclic anhydrides. Oda reported that cinchona alkaloids catalyze asymmetric methanolysis of various mono and bicyclic anhydrides. See Hiratake, J.; Yamamoto, Y.; Oada, J. *J. Chem. Soc. Chem. Commun.* 1985, 1717-1719. Atkin later extended this reaction to desymmetrize certain tricyclic anhydrides. See Aitken, R. A.; Gopal, J. *Tetrahedron: Asymmetry* 1990, 1, 517-520. Although the reactions proceeded in reasonable yield, the hemiesters were obtained in low to modest enantiomeric excess.

We hypothesized that the unsatisfactory enantioselectivity outlined above might partially arise from the existence of competing non-selective catalysis by the quinoline nitrogen because the monohydrochloride quinine is reported by Atkin to catalyze the methanolysis of the cyclic anhydride with no enantioselectivity. The quinoline-nitrogen-catalyzed stereorandom pathway should become increasingly competitive as the reaction proceeds to high conversion, while the rate of the quinuclidine-nitrogen-catalyzed enantioselective reaction is expected to decrease significantly as a result of deactivation of the catalyst caused by protonation of the quinuclidine nitrogen by the acidic hemiester product of alcoholysis.

In principle, the racemic pathway could be suppressed by using as the catalyst analogs of cinchona alkaloids lacking the quinoline nitrogen. The implementation of such an approach is, however, experimentally difficult due to the considerable synthetic effort required for the preparation of such analogs. See Pluim, H. Ph.D. Thesis, University of Groningen, Groningen, The Netherlands, 1982. Furthermore, a large, if not stoichiometric, amount of the quinuclidine catalysts may be required to promote effectively the reaction. Remarkably, we have exploited an alternative strategy of decreasing the basicity of the quinuclidine nitrogen, thereby shifting the equilibrium of the acid-base reaction towards the formation of the free amine catalyst. Our approach leads to significant improvements in both the efficiency and the selectivity of the asymmetric catalysis through minimizing the deactivation of the free base amine catalyst by the acidic hemiester. Furthermore this approach may be easily implemented experimentally by changing the environment around the quinuclidine nitrogen via a simple modification of the cinchona alkaloid.

We recognized that derivatizations of the C-9 alcohol of cinchona alkaloids with bulky substituents would generate derivatives with a decreased basicity of the quinuclidine nitrogen due to destabilization of the ammonium ion of the quinuclidine nitrogen, likely via the creation of a steric barrier for ion solvation. Accordingly, as described herein, the present invention relates to methods and monomeric catalysts for the catalytic asymmetric desymmetrization of prochiral and meso compounds and the like. The primary constituents of the methods, which are set forth in detail below, are: a non-racemic chiral monomeric catalyst derived from a single quinine or quinidine; a prochiral or meso substrate, typically a prochiral or meso cyclic anhydride; and a nucleophile, typically the solvent, which under the reaction conditions selectively attacks one of the carbonyl groups of the cyclic anhyride, generating an enantiomerically enriched chiral product. Additionally, the monomeric catalysts and methods of the present invention have been exploited to effect kinetic resolutions of racemic mixtures and the like.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderance of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A$ ($ee$)=(% Enantiomer $A$)–(% Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantiomerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

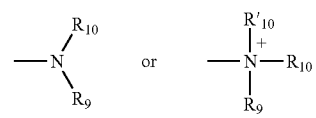

wherein $R_9$, $R_{10}$ and $R'_{10}$ each independently represent a group permitted by the rules of valence.

The term "acylamino" is art-recognized and refers to a moiety that can be represented by the general formula:

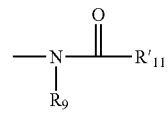

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art-recognized as an amino-substituted carbonyl and includes a moiety that can be represented by the general formula:

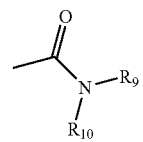

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art-recognized and includes such moieties as can be represented by the general formula:

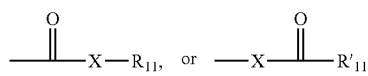

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, proploxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art-recognized and includes a moiety that can be represented by the general formula:

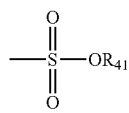

in which $R_{41}$ is an electron pair, hydrogen, alkyl, cycloalkyl, or aryl.

The term "sulfonylamino" is art-recognized and includes a moiety that can be represented by the general formula:

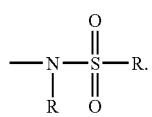

The term "sulfamoyl" is art-recognized and includes a moiety that can be represented by the general formula:

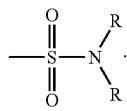

The term "sulfonyl", as used herein, refers to a moiety that can be represented by the general formula:

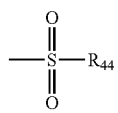

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

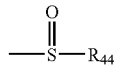

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

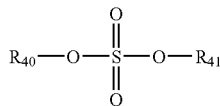

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986-87, inside cover.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The term "1-adamantyl" is art-recognized and includes a moiety represented by the formula:

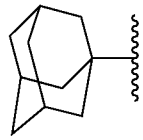

The term "(−)-menthyl" is art-recognized and includes a moiety represented by the formula:

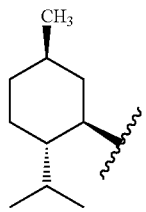

The term "(+)-menthyl" is art-recognized and includes a moiety represented by the formula:

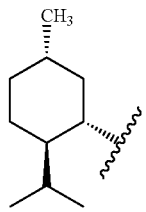

The term "isobornyl" is art-recognized and includes a moiety represented by the formula:

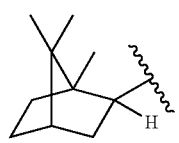

The term "isopinocamphyl" is art-recognized and includes a moiety represented by the formula:

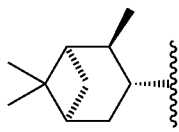

The term "(+)-fenchyl" is art-recognized and includes a moiety represented by the formula:

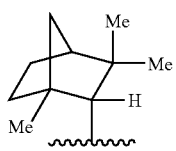

The term "QD" is represented by the formula:

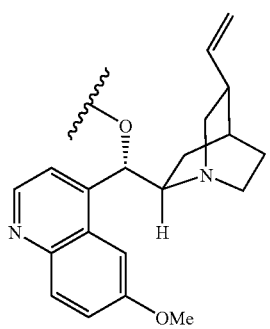

The term "Q" is represented by the formula:

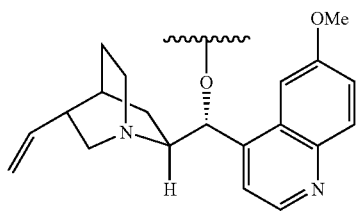

Catalysts of the Invention

The catalysts employed in the subject methods are non-racemic chiral amines which present an asymmetric environment, causing differentiation among two or more moieties related by symmetry in a prochiral or meso molecule, (i.e., a molecule comprising at least two chiral centers), both of which comprise an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity.

As mentioned above, the choice of catalyst substituents can also effect the electronic properties of the catalyst. Substitution of the catalyst with electron-rich (electron-donating) moieties (for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertiary amine nitrogen will influence the Lewis basicity of the nitrogen and its nucleophilicity. Choice of appropriate substituents thus makes possible the "tuning" of the reaction rate and the stereoselectivity of the reaction.

One aspect of the present invention relates to a compound represented by formula I:

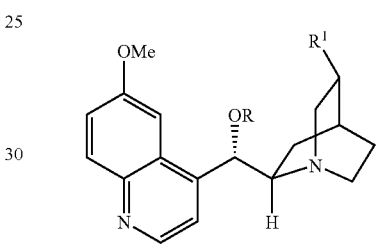

wherein

R represents —C(O)R$^2$, —(C(R$^3$)$_2$)$_n$CO$_2$R$^4$, —(C(R$^3$)$_2$)$_n$C(O)N(R$^5$)$_2$, —(C(R$^3$)$_2$)$_n$CN, —(C(R$^3$)$_2$)$_n$C(O)R$^5$, —C(C(R$^3$)$_2$)$_n$C≡CR$^6$, —(C(R$^3$)$_2$)$_n$OPO(OR$^5$)$_2$, —(C(R$^3$)$_2$)$_n$OR$^5$, —(C(R$^3$)$_2$)$_n$N(R$^5$)$_2$, —(C(R$^3$)$_2$)$_n$SR$^5$, or —(C(R$^3$)$_2$)$_n$NO$_2$;

R$^1$ represents alkyl or alkenyl;

R$^2$ represents alkyl, cycloalkyl, or alkenyl;

R$^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$^4$ represents cycloalkyl, —CH(R$^3$)$_2$, alkenyl, alkynyl, aryl, or aralkyl;

R$^5$ represents independently for each occurrence H, alkyl, alkenyl, aryl, cycloalkyl, or aralkyl;

R$^6$ represents optionally substituted alkyl, alkenyl, aryl, or aralkyl; and n is 1-10.

In certain embodiments, the compounds of the present invention are represented by formula I, wherein R represents —C(O)R$^2$, —(C(R$^3$)$_2$)$_n$CO$_2$R$^4$, —(C(R$^3$)$_2$)$_n$C(O)N(R$^5$)$_2$—(C(R$^3$)$_2$)$_n$CN, —(C(R$^3$)$_2$)$_n$C(O)R$^5$, or —C(C(R$^3$)$_2$)$_n$C≡CR$^6$.

In certain embodiments, the compounds of the present invention are represented by formula I, wherein R$^1$ is ethyl.

In certain embodiments, the compounds of the present invention are represented by formula I, wherein R$^1$ is —CH═CH$_2$.

In certain embodiments, the compounds of the present invention are represented by formula I, wherein R is —C(O)R².

In certain embodiments, the compounds of the present invention are represented by formula I, wherein R is —C(O)R² and R² is alkyl.

In certain embodiments, the compounds of the present invention are represented by formula I, wherein R is —(C(R³)₂)ₙCO₂R⁴.

In certain embodiments, the compounds of the present invention are represented by formula I, wherein R is —(C(R³)₂)ₙCO₂R⁴ and R⁴ is —CH(R³)₂.

In certain embodiments, the compounds of the present invention are represented by formula I, wherein R is —(C(R³)₂)ₙCO₂R⁴, R⁴ is —CH(R³)₂, n is 1.

In certain embodiments, the compounds of the present invention are represented by formula I, wherein R is —(C(R³)₂)ₙCO₂R⁴ and R⁴ is cycloalkyl.

In certain embodiments, the compounds of the present invention are represented by formula I, wherein R is —CH₂CO₂R⁴ and R⁴ is cycloalkyl.

In certain embodiments, the compounds of the present invention are represented by formula I, wherein R is —CH₂CO₂R⁴, R⁴ is cyclohexyl; and R¹ is —CH=CH₂.

In certain embodiments, the compounds of the present invention are represented by formula I, wherein R is —CH₂CO₂R⁴; R⁴ is (−)-menthyl, 1-adamantyl, isobornyl, (−)-isopinocamphyl, or (+)-fenchyl; and R¹ is —CH=CH₂.

In certain embodiments, the compounds of the present invention are represented by formula I, wherein R is —(C(R³)₂)ₙC(O)N(R⁵)₂.

In certain embodiments, the compounds of the present invention are represented by formula I, wherein R is —CH₂C(O)N(R⁵)₂ and R¹ is —CH=CH₂.

In certain embodiments, the compounds of the present invention are represented by formula I, wherein R is —CH₂C(O)NH-1-adamantyl and R¹ is —CH=CH₂.

In certain embodiments, the compounds of the present invention are represented by formula I, wherein R is —(C(R³)₂)ₙCN.

In certain embodiments, the compounds of the present invention are represented by formula I, wherein R is —CH₂CN and R¹ is —CH=CH₂.

In certain embodiments, the compounds of the present invention are represented by formula I, wherein R is —(C(R³)₂)ₙCOR⁵.

In certain embodiments, the compounds of the present invention are represented by formula I, wherein R is —CH₂C(O)R⁵ and R⁵ is alkyl.

In certain embodiments, the compounds of the present invention are represented by formula I, wherein R is —CH₂C(O)C(CH₃)₃ and R¹ is —CH=CH₂.

In certain embodiments, said compound is QD-IP, QD-PC, QD-AD, QD-(−)-MN, QD-(+)-MN, QD-AC, QD-Piv, QD-PH, QD-AN, QD-NT, QD-CN, QD-CH, QD-IB, QD-EF, QD-AA, QD-MP, or QD-IPC.

In certain embodiments, said compound is QD-IP, QD-(−)-MN, or QD-AD.

Another aspect of the present invention relates to a compound represented by formula II:

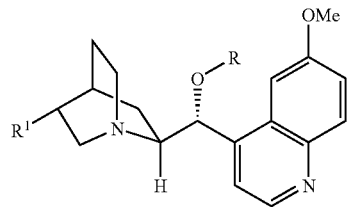

wherein

R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, —C(C(R³)₂)ₙC=CR⁶, —(C(R³)₂)ₙOPO(OR⁵)₂, —(C(R³)₂)ₙOR⁵, —(C(R³)₂)ₙN(R⁵)₂, —(C(R³)₂)ₙSR⁵, or —(C(R³)₂)ₙNO₂;

R¹ represents alkyl or alkenyl;

R² represents alkyl, cycloalkyl, or alkenyl;

R³ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R⁴ represents cycloalkyl, —CH(R³)₂, alkenyl, alkynyl, aryl, or aralkyl;

R⁵ represents independently for each occurrence H, alkyl, alkenyl, aryl, cycloalkyl, or aralkyl;

R⁶ represents optionally substituted alkyl, alkenyl, aryl, or aralkyl; and n is 1-10.

In certain embodiments, said compound is Q-IP, Q-PC, Q-AD, Q-(−)-MN, Q-(+)-MN, Q-AC, Q-Piv, Q-PH, Q-AN, Q-NT, Q-CN, Q-CH, Q-IB, Q-EF, Q-AA, Q-MP, or Q-IPC.

Methods of the Invention—Preparation of Asymmetric Tertiary Amine-Containing Catalysts One aspect of the invention relates to a method of preparing a derivatized cinchona alkaloid catalyst as depicted in Scheme 1:

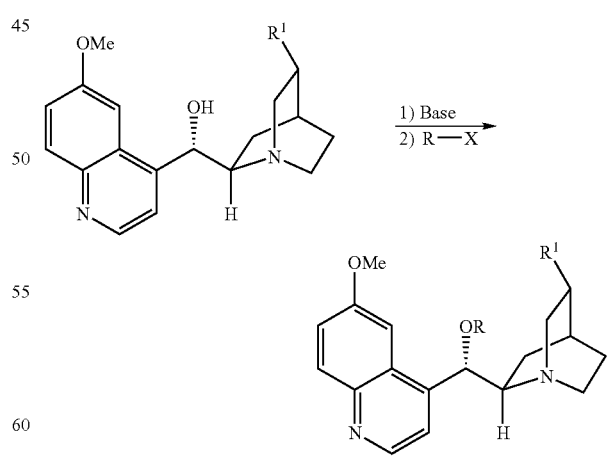

wherein,

X represents Cl, Br, I, OSO₂CH₃, or OSO₂CF₃;

R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, —C(C $(R^3)_2)_nC\equiv CR^6$, $-(C(R^3)_2)_nOPO(OR^5)_2$, $-(C(R^3)_2)_nOR^5$, $-(C(R^3)_2)_nN(R^5)_2$, $-(C(R^3)_2)_nSR^5$, or $-(C(R^3)_2)_nNO_2$;

$R^1$ represents alkyl or alkenyl;

$R^2$ represents alkyl, cycloalkyl, or alkenyl;

$R^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R^4$ represents cycloalkyl, $-CH(R^3)_2$, alkenyl, alkynyl, aryl, or aralkyl;

$R^5$ represents independently for each occurrence H, alkyl, alkenyl, aryl, cycloalkyl, or aralkyl;

$R^6$ represents optionally substituted alkyl, alkenyl, aryl, or aralkyl;

n is 1-10; and base is a Bronsted base.

In certain embodiments, the present invention relates to the aforementioned method, wherein X is Cl or Br.

In certain embodiments, the present invention relates to the aforementioned method, wherein said base is a metal hydride, alkoxide, or amide, or carbanion.

In certain embodiments, the present invention relates to the aforementioned method, wherein said base is $NaH$, $CaH_2$, KH, or Na.

In certain embodiments, the present invention relates to the aforementioned method, wherein R represents $-C(O)R^2$, $-(C(R^3)_2)_nCO_2R^4$, $-(C(R^3)_2)_nC(O)N(R^5)_2$, $-(C(R^3)_2)_nCN$, $-(C(R^3)_2)_nC(O)R^5$, or $-C((R^3)_2)_nC\equiv CR^6$.

In certain embodiments, the present invention relates to the aforementioned method, wherein $R^1$ is ethyl.

In certain embodiments, the present invention relates to the aforementioned method, wherein $R^1$ is $-CH=CH_2$.

In certain embodiments, the present invention relates to the aforementioned method, wherein R is $-C(O)R^2$.

In certain embodiments, the present invention relates to the aforementioned method, wherein R is $-C(O)R^2$ and $R^2$ is alkyl.

In certain embodiments, the present invention relates to the aforementioned method, wherein R is $-C(O)C(CH_3)_3$ and $R^1$ is $-CH=CH_2$.

In certain embodiments, the present invention relates to the aforementioned method, wherein R is $-(C(R^3)_2)_nCO_2R^4$.

In certain embodiments, the present invention relates to the aforementioned method, wherein R is $-(C(R^3)_2)_nCO_2R^4$ and $R^4$ is $-CH(R^3)_2$.

In certain embodiments, the present invention relates to the aforementioned method, wherein R is $-(C(R^3)_2)_nCO_2R^4$, $R^4$ is $-CH(R^3)_2$, n is 1.

In certain embodiments, the present invention relates to the aforementioned method, wherein R is $-CH_2CO_2CH(CH_3)_2$. and $R^1$ is $-CH=CH_2$.

In certain embodiments, the present invention relates to the aforementioned method, wherein R is $-CH_2CO_2CH_2CH(CH_3)_2$ and $R^1$ is $-CH=CH_2$. In certain embodiments, the present invention relates to the aforementioned method, wherein R is $-(C(R^3)_2)_nCO_2R^4$ and $R^4$ is cycloalkyl.

In certain embodiments, the present invention relates to the aforementioned method, wherein R is $-CH_2CO_2R^4$ and $R^4$ is cycloalkyl.

In certain embodiments, the present invention relates to the aforementioned method, wherein R is $-CH_2CO_2R^4$, $R^4$ is cyclohexyl; and $R^1$ is $-CH=CH_2$.

In certain embodiments, the present invention relates to the aforementioned method, wherein R is $-CH_2CO_2R^4$; $R^4$ is (−)-menthyl, 1-adamantyl, isobornyl, (−)-isopinocamphyl, or (+)-fenchyl; and $R^1$ is $-CH=CH_2$.

In certain embodiments, the present invention relates to the aforementioned method, wherein R is $-CH_2CO_2R^4$; $R^4$ is (−)-menthyl or 1-adamantyl; and $R^1$ is $-CH=CH_2$.

In certain embodiments, the present invention relates to the aforementioned method, wherein R is $-(C(R^3)_2)_nC(O)N(R^5)_2$.

In certain embodiments, the present invention relates to the aforementioned method, wherein R is $-CH_2C(O)N(R^5)_2$ and $R^1$ is $-CH=CH_2$.

In certain embodiments, the present invention relates to the aforementioned method, wherein R is $-CH_2C(O)NH$-1-adamantyl and $R^1$ is $-CH=CH_2$.

In certain embodiments, the present invention relates to the aforementioned method, wherein R is $-(C(R^3)_2)_nCN$.

In certain embodiments, the present invention relates to the aforementioned method, wherein R is $-CH_2CN$ and $R^1$ is $-CH=CH_2$.

In certain embodiments, the present invention relates to the aforementioned method, wherein R is $-(C(R^3)_2)_nC(O)R^5$.

In certain embodiments, the present invention relates to the aforementioned method, wherein R is $-CH_2C(O)R^5$ and $R^5$ is alkyl.

In certain embodiments, the present invention relates to the aforementioned method, wherein R is $-CH_2C(O)C(CH_3)_3$ and R1 is $-CH=CH_2$.

In certain embodiments, the present invention relates to the aforementioned method, wherein said catalyst is QD-IP, QD-PC, QD-AD, QD-(−)-MN, QD-(+)-MN, QD-AC, QD-Piv, QD-PH, QD-AN, QD-NT, QD-CN, QD-CH, QD-IB, QD-EF, QD-AA, QD-MP, or QD-IPC.

In certain embodiments, the present invention relates to the aforementioned method, wherein said catalyst is QD-IP, QD-(−)-MN, or QD-AD.

Another aspect of the invention relates to a method of preparing a derivatized cinchona alkaloid catalyst as depicted in Scheme 2:

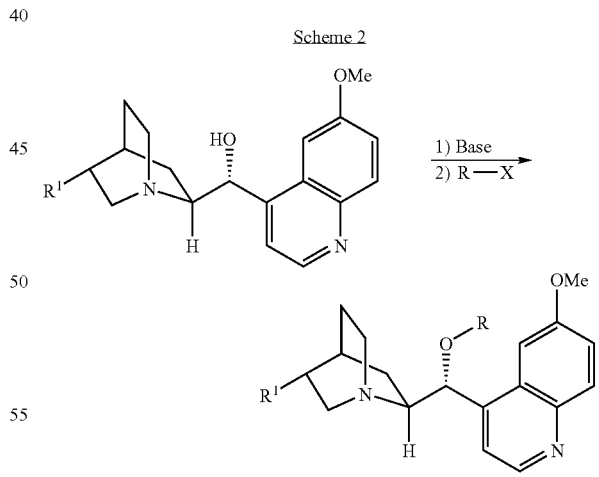

wherein,

X represents Cl, Br, I, $OSO_2CH_3$, or $OSO_2CF_3$;

R represents $-C(O)R^2$, $-(C(R^3)_2)_nCO_2R^4$, $-(C(R^3)_2)_nC(O)N(R^5)_2$, $-(C(R^3)_2)_nCN$, $-(C(R^3)_2)_nC(O)R^5$, $-C(C(R^3)_2)_nC\equiv CR^6$, $-(C(R^3)_2)_nOPO(OR^5)_2$, $-(C(R^3)_2)_nN(R^5)_2$, $-(C(R^3)_2)_nSR^5$, or $-(C(R^3)_2)_nNO_2$;

$R^1$ represents alkyl or alkenyl;

$R^2$ represents alkyl, cycloalkyl, or alkenyl;

$R^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R^4$ represents cycloalkyl, —$CH(R^3)_2$, alkenyl, alkynyl, aryl, or aralkyl;

$R^5$ represents independently for each occurrence H, alkyl, alkenyl, aryl, cycloalkyl, or aralkyl;

$R^6$ represents optionally substituted alkyl, alkenyl, aryl, or aralkyl;

n is 1-10; and base is a Bronsted base.

In certain embodiments, the present invention relates to the aforementioned method, wherein said catalyst is Q-IP, Q-PC, Q-AD, Q-(−)-MN, Q-(+)-MN, Q-AC, Q-Piv, Q-PH, Q-AN, Q-NT, Q-CN, Q-CH, Q-IB, Q-EF, Q-AA, Q-MP, or Q-IPC.

Methods of the Invention—Catalyzed Reactions

In one aspect of the present invention there is provided a process for stereoselectively producing compounds with at least one stereogenic center from prochiral, meso or racemic starting materials. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective ring opening process which comprises combining a nucleophilic reactant, a prochiral or chiral cyclic substrate, and at least a catalytic amount of non-racemic chiral catalyst of particular characteristics (as described below). The cyclic substrate of the reaction will include a carbocycle or heterocycle which has an electrophilic atom susceptible to attack by the nucleophile. The combination is maintained under conditions appropriate for the chiral catalyst to catalyze stereoselective opening of the cyclic substrate at the electrophilic atom by reaction with the nucleophilic reactant. This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

The processes of this invention can provide optically active products with very high stereoselectivity (e.g., enantioselectivity or diastereoselectivity) or regioselectivity. In preferred embodiments of the subject desymmetrization reactions, products with enantiomeric excesses of greater than about 50%, greater than about 70%, greater than about 90%, and most preferably greater than about 95% can be obtained. The processes of this invention can also be carried out under reaction conditions suitable for commercial use, and typically proceed at reaction rates suitable for large scale operations.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include esterification, N-alkylation of amides, and the like. The invention expressly contemplates the preparation of end-products and synthetic intermediates which are useful for the preparation or development or both of cardiovascular drugs, non-steroidal anti-inflammatory drugs, central nervous system agents, and antihistaminics.

One aspect of the present invention relates to a method of preparing a chiral, non-racemic compound from a prochiral cyclic anhydride or a meso cyclic anhydride, comprising the step of:

reacting a prochiral cyclic anhydride or a meso cyclic anhydride with a nucleophile in the presence of a catalyst; wherein said prochiral cyclic anhydride or meso cyclic anhydride comprises an internal plane of symmetry or point of symmetry or both; thereby producing a chiral, non-racemic compound; wherein said catalyst is represented by formula I:

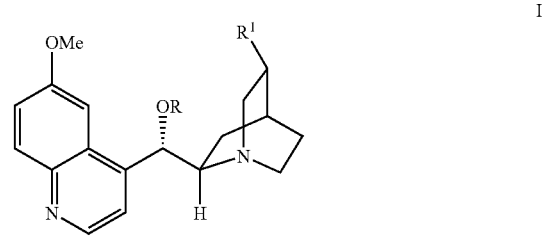

wherein

R represents —$C(O)R^2$, —$(C(R^3)_2)_nCO_2R^4$, —$(C(R^3)_2)_nC(O)N(R^5)_2$, —$(C(R^3)_2)_nCN$, —$(C(R^3)_2)_nC(O)R^5$, —$C(C(R^3)_2)_nC\!\!\equiv\!\!CR^6$, —$(C(R^3)_2)_nOPO(OR^5)_2$, —$(C(R^3)_2)_nOR^5$, —$(C(R^3)_2)_nN(R^5)_2$, —$(C(R^3)_2)_nSR^5$, or —$(C(R^3)_2)_nNO_2$;

$R^1$ represents alkyl or alkenyl;

$R^2$ represents alkyl, cycloalkyl, or alkenyl;

$R^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R^4$ represents cycloalkyl, —$CH(R^3)_2$, alkenyl, alkynyl, aryl, or aralkyl;

$R^5$ represents independently for each occurrence H, alkyl, alkenyl, aryl, cycloalkyl, or aralkyl;

$R^6$ represents optionally substituted alkyl, alkenyl, aryl, or aralkyl; and n is 1-10.

In certain embodiments, the present invention relates to the aforementioned method, wherein R represents —$C(O)R^2$, —$(C(R^3)_2)_nCO_2R^4$, —$(C(R^3)_2)_nC(O)N(R^5)_2$, —$(C(R^3)_2)_nCN$, —$(C(R^3)_2)_nC(O)R^5$, or —$C(C(R^3)_2)_nC\!\!\equiv\!\!CR^6$.

In certain embodiments, the present invention relates to the aforementioned method, wherein $R^1$ is ethyl.

In certain embodiments, the present invention relates to the aforementioned method, wherein $R^1$ is —$CH\!\!=\!\!CH_2$. In certain embodiments, the present invention relates to the aforementioned method, wherein R is —$C(O)R^2$.

In certain embodiments, the present invention relates to the aforementioned method, wherein R is —$C(O)R^2$ and $R^2$ is alkyl.

In certain embodiments, the present invention relates to the aforementioned method, wherein R is —$(C(R^3)_2)_nCO_2R^4$.

In certain embodiments, the present invention relates to the aforementioned method, wherein R is —$(C(R^3)_2)_nCO_2R^4$ and $R^4$ is —$CH(R^3)_2$.

In certain embodiments, the present invention relates to the aforementioned method, wherein R is —$(C(R^3)_2)_nCO_2R^4$, $R^4$ is —$CH(R^3)_2$, n is 1.

In certain embodiments, the present invention relates to the aforementioned method, wherein R is —$(C(R^3)_2)_nCO_2R^4$ and $R^4$ is cycloalkyl.

In certain embodiments, the present invention relates to the aforementioned method, wherein R is —CH$_2$CO$_2$R$^4$ and R$^4$ is cycloalkyl.

In certain embodiments, the present invention relates to the aforementioned method, wherein R is —CH$_2$CO$_2$R$^4$, R$^4$ is cyclohexyl; and R$^1$ is —CH=CH$_2$.

In certain embodiments, the present invention relates to the aforementioned method, wherein R is —CH$_2$CO$_2$R$^4$; R$^4$ is (−)-menthyl, 1-adamantyl, isobornyl, (−)-isopinocamphyl, or (+)-fenchyl; and R$^1$ is —CH=CH$_2$.

In certain embodiments, the present invention relates to the aforementioned method, wherein R is —(C(R$^3$)$_2$)$_n$C(O)N(R$^5$)$_2$.

In certain embodiments, the present invention relates to the aforementioned method, wherein R is —CH$_2$C(O)N(R$^5$)$_2$ and R$^1$ is —CH=CH$_2$.

In certain embodiments, the present invention relates to the aforementioned method, wherein R is —CH$_2$C(O)NH-1-adamantyl and R$^1$ is —CH=CH$_2$.

In certain embodiments, the present invention relates to the aforementioned method, wherein R is —(C(R$^3$)$_2$)$_n$CN.

In certain embodiments, the present invention relates to the aforementioned method, wherein R is —CH$_2$CN and R$^1$ is CH=CH$_2$.

In certain embodiments, the present invention relates to the aforementioned method, wherein R is —(C(R$^3$)$_2$)$_n$C(O)R$^5$.

In certain embodiments, the present invention relates to the aforementioned method, wherein R is —CH$_2$C(O)R$^5$ and R$^5$ is alkyl.

In certain embodiments, the present invention relates to the aforementioned method, wherein R is —CH$_2$C(O)C(CH$_3$)$_3$ and R$^1$ is —CH=CH$_2$.

In certain embodiments, the present invention relates to the aforementioned method, wherein said catalyst is QD-IP, QD-PC, QD-AD, QD-(−)-MN, QD-(+)-MN, QD-AC, QD-Piv, QD-PH, QD-AN, QD-NT, QD-CN, QD-CH, QD-IB, QD-EF, QD-AA, QD-MP, or QD-IPC.

In certain embodiments, the present invention relates to the aforementioned method, wherein said catalyst is QD-IP, QD-(−)-MN, or QD-AD.

In certain embodiments, the present invention relates to the aforementioned method, wherein said nucleophile is an alcohol.

In certain embodiments, the present invention relates to the aforementioned method, wherein said nucleophile is a primary alcohol.

In certain embodiments, the present invention relates to the aforementioned method, wherein said nucleophile is a methanol or CF$_3$CH$_2$OH.

In certain embodiments, the present invention relates to the aforementioned method, wherein said prochiral cyclic anhydride or meso cyclic anhydride is a substituted succinic anhydride or a substituted glutaric anhydride.

In certain embodiments, the present invention relates to the aforementioned method, wherein said catalyst is present in less than about 70 mol % relative to said prochiral cyclic anhydride or meso cyclic anhydride.

In certain embodiments, the present invention relates to the aforementioned method, wherein said catalyst is present in less than about 40 mol % relative to said prochiral cyclic anhydride or meso cyclic anhydride.

In certain embodiments, the present invention relates to the aforementioned method, wherein said catalyst is present in less than about 10 mol % relative to said prochiral cyclic anhydride or meso cyclic anhydride.

In certain embodiments, the present invention relates to the aforementioned method, wherein said chiral, non-racemic compound has an enantiomeric excess greater than about 50%.

In certain embodiments, the present invention relates to the aforementioned method, wherein said chiral, non-racemic compound has an enantiomeric excess greater than about 70%.

In certain embodiments, the present invention relates to the aforementioned method, wherein said chiral, non-racemic compound has an enantiomeric excess greater than about 90%.

In certain embodiments, the present invention relates to the aforementioned method, wherein said chiral, non-racemic compound has an enantiomeric excess greater than about 95%.

In certain embodiments, the present invention relates to the aforementioned method, wherein R is —CH$_2$CO$_2$R$^4$; R$^4$ is (−)-menthyl, 1-adamantyl, isobornyl, (−)-isopinocamphyl, or (+)-fenchyl; R$^1$ is —CH=CH$_2$; and said nucleophile is an alcohol.

In certain embodiments, the present invention relates to the aforementioned method, wherein R is —CH$_2$CO$_2$R$^4$; R$^4$ is (−)-menthyl or 1-adamantyl; R$^1$ is —CH=CH$_2$; and said nucleophile is an alcohol.

In certain embodiments, the present invention relates to the aforementioned method, wherein R is —CH$_2$CO$_2$R$^4$; R$^4$ is (−)-menthyl or 1-adamantyl; R$^1$ is —CH=CH$_2$; and said nucleophile is methanol or CF$_3$CH$_2$OH.

Another aspect of the present invention relates to a method of preparing a chiral, non-racemic compound from a prochiral cyclic anhydride or a meso cyclic anhydride, comprising the step of:

reacting a prochiral cyclic anhydride or a meso cyclic anhydride with a nucleophile in the presence of a catalyst; wherein said prochiral cyclic anhydride or meso cyclic anhydride comprises an internal plane of symmetry or point of symmetry or both; thereby producing a chiral, non-racemic compound; wherein said catalyst is represented by formula II:

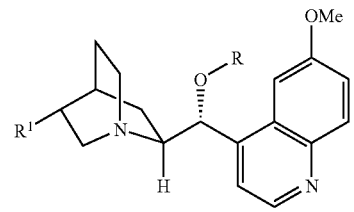

wherein

R represents —C(O)R$^2$, —(C(R$^3$)$_2$)$_n$CO$_2$R$^4$, —(C(R$^3$)$_2$)$_n$C(O)N(R$^5$)$_2$, —(C(R$^3$)$_2$)$_n$CN, —(C(R$^3$)$_2$)$_n$C(O)R$^5$, —C(C(R$^3$)$_2$)$_n$C=CR$^6$, —(C(R$^3$)$_2$)$_n$OPO(OR$^5$)$_2$, —(C(R$^3$)$_2$)$_n$OR$^5$, —(C(R$^3$)$_2$)$_n$N(R$^5$)$_2$, —(C(R$^3$)$_2$)$_n$SR$^5$, or —(C(R$^3$)$_2$)$_n$NO$_2$;

R$^1$ represents alkyl or alkenyl;

R$^2$ represents alkyl, cycloalkyl, or alkenyl;

R$^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$^4$ represents cycloalkyl, —CH(R$^3$)$_2$, alkenyl, alkynyl, aryl, or aralkyl;

$R^5$ represents independently for each occurrence H, alkyl, alkenyl, aryl, cycloalkyl, or aralkyl;

$R^6$ represents optionally substituted alkyl, alkenyl, aryl, or aralkyl; and n is 1-10.

In certain embodiments, said catalyst is Q-IP, Q-PC, Q-AD, Q-(−)-MN, Q-(+)-MN, Q-AC, Q-Piv, Q-PH, Q-AN, Q-NT, Q-CN, Q-CH, Q-IB, Q-EF, Q-AA, Q-MP, or Q-IPC.

In certain embodiments, the present invention relates to the aforementioned method, wherein said nucleophile is an alcohol.

In certain embodiments, the present invention relates to the aforementioned method, wherein said nucleophile is a primary alcohol.

In certain embodiments, the present invention relates to the aforementioned method, wherein said nucleophile is methanol or $CF_3CH_2OH$.

In certain embodiments, the present invention relates to the aforementioned method, wherein said prochiral cyclic anhydride or meso cyclic anhydride is a substituted succinic anhydride or a substituted glutaric anhydride.

In certain embodiments, the present invention relates to the aforementioned method, wherein said catalyst is present in less than about 70 mol % relative to said prochiral cyclic anhydride or meso cyclic anhydride.

In certain embodiments, the present invention relates to the aforementioned method, wherein said catalyst is present in less than about 40 mol % relative to said prochiral cyclic anhydride or meso cyclic anhydride.

In certain embodiments, the present invention relates to the aforementioned method, wherein said catalyst is present in less than about 10 mol % relative to said prochiral cyclic anhydride or meso cyclic anhydride.

In certain embodiments, the present invention relates to the aforementioned method, wherein said chiral, non-racemic compound has an enantiomeric excess greater than about 50%.

In certain embodiments, the present invention relates to the aforementioned method, wherein said chiral, non-racemic compound has an enantiomeric excess greater than about 70%.

In certain embodiments, the present invention relates to the aforementioned method, wherein said chiral, non-racemic compound has an enantiomeric excess greater than about 90%.

In certain embodiments, the present invention relates to the aforementioned method, wherein said chiral, non-racemic compound has an enantiomeric excess greater than about 95%.

In certain embodiments, the present invention relates to the aforementioned method, wherein R is $-CH_2CO_2R^4$; $R^4$ is (−)-menthyl, 1-adamantyl, isobornyl, (−)-isopinocamphyl, or (+)-fenchyl; $R^1$ is $-CH=CH_2$; and said nucleophile is an alcohol.

In certain embodiments, the present invention relates to the aforementioned method, wherein R is $-CH_2CO_2R^4$; $R^4$ is (−)-menthyl or 1-adamantyl; $R^1$ is $-CH=CH_2$; and said nucleophile is an alcohol.

In certain embodiments, the present invention relates to the aforementioned method, wherein R is $-CH_2CO_2R^4$; $R^4$ is (−)-menthyl or 1-adamantyl; $R^1$ is $-CH=CH_2$; and said nucleophile is methanol or $CF_3CH_2OH$.

Methods of Invention—Kinetic Resolution

In another aspect of the present invention, kinetic resolution of enantiomers occurs by catalysis, using a subject chiral catalyst, of the tranformation of a racemic substrate. In the subject kinetic resolution processes for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than the expensive, enantiomerically pure starting compounds. In certain embodiments, the subject catalysts may be used in kinetic resolutions of racemic cyclic substrates wherein the nucleophile is a co-solvent. Suitable nucleophiles of this type include water, alcohols, and thiols.

One aspect of the present invention relates to a method of kinetic resolution, comprising the step of:

reacting a racemic cyclic anhydride with an alcohol in the presence of a catalyst represented by formula I:

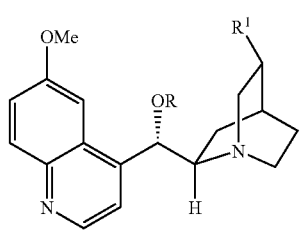

wherein

R represents $-C(O)R^2$, $-(C(R^3)_2)_nCO_2R^4$, $-(C(R^3)_2)_nC(O)N(R^5)_2$, $-(C(R^3)_2)_nCN$, $-(C(R^3)_2)_nC(O)R^5$, $-C(C(R^3)_2)_nC=CR^6$, $-(C(R^3)_2)_nOPO(OR^5)_2$, $-(C(R^3)_2)_nOR^5$, $-(C(R^3)_2)_nN(R^5)_2$, $-(C(R^3)_2)_nSR^5$, or $-(C(R^3)_2)_nNO_2$;

$R^1$ represents alkyl or alkenyl;

$R^2$ represents alkyl, cycloalkyl, or alkenyl;

$R^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R^4$ represents cycloalkyl, $-CH(R^3)_2$, alkenyl, alkynyl, aryl, or aralkyl;

$R^5$ represents independently for each occurrence H, alkyl, alkenyl, aryl, cycloalkyl, or aralkyl;

$R^6$ represents optionally substituted alkyl, alkenyl, aryl, or aralkyl;

n is 1-10; and when said method of kinetic resolution is completed or interrupted any unreacted cyclic anhydride has an enantiomeric excess greater than zero and the enantiomeric excess of the product is greater than zero.

In certain embodiments, the present invention relates to the aforementioned method, wherein R represents $-C(O)R^2$, $-(C(R^3)_2)_nCO_2R^4$, $-(C(R^3)_2)_nC(O)N(R^5)_2$, $-(C(R^3)_2)_nCN$, $-(C(R^3)_2)_nC(O)R^5$, or $-C(C(R^3)_2)_nC=CR^6$.

In certain embodiments, the present invention relates to the aforementioned method, wherein $R^1$ is ethyl.

In certain embodiments, the present invention relates to the aforementioned method, wherein $R^1$ is $-CH=CH_2$.

In certain embodiments, the present invention relates to the aforementioned method, wherein R is $-C(O)R^2$.

In certain embodiments, the present invention relates to the aforementioned method, wherein R is —C(O)R² and R² is alkyl.

In certain embodiments, the present invention relates to the aforementioned method, wherein R is —(C(R³)₂)ₙCO₂R⁴.

In certain embodiments, the present invention relates to the aforementioned method, wherein R is —(C(R³)₂)ₙCO₂R⁴ and R⁴ is —CH(R³)₂.

In certain embodiments, the present invention relates to the aforementioned method, wherein R is —(C(R³)₂)ₙCO₂R⁴, R⁴ is —CH(R³)₂, n is 1.

In certain embodiments, the present invention relates to the aforementioned method, wherein R is —(C(R³)₂)ₙCO₂R⁴ and R⁴ is cycloalkyl.

In certain embodiments, the present invention relates to the aforementioned method, wherein R is —CH₂CO₂R⁴ and R⁴ is cycloalkyl.

In certain embodiments, the present invention relates to the aforementioned method, wherein R is —CH₂CO₂R⁴, R⁴ is cyclohexyl; and R¹ is —CH═CH₂.

In certain embodiments, the present invention relates to the aforementioned method, wherein R is —CH₂CO₂R⁴; R⁴ is (−)-menthyl, 1-adamantyl, isobornyl, (−)-isopinocamphyl, or (+)-fenchyl; and R¹ is —CH═CH₂.

In certain embodiments, the present invention relates to the aforementioned method, wherein R is —(C(R³)₂)ₙC(O)N(R⁵)₂.

In certain embodiments, the present invention relates to the aforementioned method, wherein R is —CH₂C(O)N(R⁵)₂ and R¹ is —CH═CH₂.

In certain embodiments, the present invention relates to the aforementioned method, wherein R is —CH₂C(O)NH-1-adamantyl and R¹ is —CH═CH₂.

In certain embodiments, the present invention relates to the aforementioned method, wherein R is —(C(R³)₂)ₙCN.

In certain embodiments, the present invention relates to the aforementioned method, wherein R is —CH₂CN and R¹ is CH═CH₂.

In certain embodiments, the present invention relates to the aforementioned method, wherein R is —(C(R³)₂)ₙCOR⁵.

In certain embodiments, the present invention relates to the aforementioned method, wherein R is —CH₂C(O)R⁵ and R⁵ is alkyl.

In certain embodiments, the present invention relates to the aforementioned method, wherein R is —CH₂C(O)C(CH₃)₃ and R¹ is —CH═CH₂.

In certain embodiments, the present invention relates to the aforementioned method, wherein said catalyst is QD-IP, QD-PC, QD-AD, QD-(−)-MN, QD-(+)-MN, QD-AC, QD-Piv, QD-PH, QD-AN, QD-NT, QD-CN, QD-CH, QD-IB, QD-EF, QD-AA, QD-MP, or QD-IPC.

In certain embodiments, the present invention relates to the aforementioned method, wherein said catalyst is QD-IP, QD-(−)-MN, or QD-AD.

In certain embodiments, the present invention relates to the aforementioned method, wherein said alcohol is a primary alcohol.

In certain embodiments, the present invention relates to the aforementioned method, wherein said nucleophile is methanol or CF₃CH₂OH.

Another aspect of the present invention relates to a method of kinetic resolution, comprising the step of:

reacting a racemic cyclic anhydride with an alcohol in the presence of a catalyst represented by formula II:

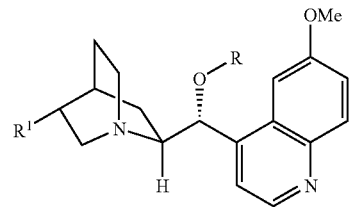

wherein

R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, —C(C(R³)₂)ₙC═CR⁶, —(C(R³)₂)ₙOPO(OR⁵)₂, —(C(R³)₂)ₙOR⁵, —(C(R³)₂)ₙN(R⁵)₂, —(C(R³)₂)ₙSR⁵, or —(C(R³)₂)ₙNO₂;

R¹ represents alkyl or alkenyl;

R² represents alkyl, cycloalkyl, or alkenyl;

R³ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R⁴ represents cycloalkyl, —CH(R³)₂, alkenyl, alkynyl, aryl, or aralkyl;

R⁵ represents independently for each occurrence H, alkyl, alkenyl, aryl, cycloalkyl, or aralkyl;

R⁶ represents optionally substituted alkyl, alkenyl, aryl, or aralkyl; and n is 1-10; and when said method of kinetic resolution is completed or interrupted any unreacted cyclic anhydride has an enantiomeric excess greater than zero and the enantiomeric excess of the product is greater than zero.

In certain embodiments, said catalyst is Q-IP, Q-PC, Q-AD, Q-(−)-MN, Q-(+)-MN, Q-AC, Q-Piv, Q-PH, Q-AN, Q-NT, Q-CN, Q-CH, Q-IB, Q-EF, Q-AA, Q-MP, or Q-IPC.

In certain embodiments, the present invention relates to the aforementioned method, wherein said alcohol is a primary alcohol.

In certain embodiments, the present invention relates to the aforementioned method, wherein said nucleophile is methanol or CF₃CH₂OH.

Nucleophiles

Nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art. For nucleophiles which exist as anions, the counterion can be any of a variety of conventional cations, including alkali and alkaline earth metal cations and ammonium cations. In certain embodiments, the nucleophile may be part of the substrate, thus resulting in an intramolecular reaction.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least a pair of reactive electrophilic centers or moieties related by an internal plane or point of symmetry at which a nucleophile may attack with the assistance of the catalyst. The catalyzed, stereoselective attack of the nucleophile at one of these electrophilic centers will produce a chiral non-racemic product. Most of the substrates contemplated for use in the methods of the present invention contain at least one ring having three to seven atoms. Small rings are frequently strained, enhancing their reactivity. However, in some embodiments a cyclic substrate may not be strained, and may have a larger electrophilic ring. Examples of suitable cyclic substrates which can be opened in the subject method include cyclic anhydrides, cyclic imides, and the like.

In preferred embodiments, the cyclic substrate is a prochiral or meso compound. In other embodiments, the cyclic substrate will be a chiral compound. In certain embodiments, the substrate will be a racemic mixture. In certain embodiments, the substrate will be a mixture of diastereomers. In certain embodiments, the methods of the present invention effect a kinetic resolution. In certain embodiments, the methods of the present invention effect a dynamic kinetic resolution. In certain embodiments, the electrophilic atom may be a heteroatom.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of $-78°$ C. to $100°$ C., more preferably in the range $-20°$ C. to $50°$ C. and still more preferably in the range $-20°$ C. to $25°$ C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

Enantioselective Alcoholysis

A wide variety of catalysts derived from modified cinchona alkaloids were examined with substituted succinic anhydrides and substituted glutaric anhydrides and the results are summarized in FIGS. 1-25. The application of catalytst QD-(−)-MN for the desymmetrization of cis-1,3-dibenzyl-tetrahydro-2H-furo[3,4-d]imidazole-2,4,6-trione is also demonstrated, which could be important for the synthesis of biotin. The catalyst is also shown to be easily recyclable in greater than 95% yield using an extraction procedure.

Summarized in FIGS. 1 and 2 are the results of a study on the comparison of the efficiency of various catalysts for methanolysis of 2,3-dimethylsuccinic anhydride in $Et_2O$ at 0.02 M concentration at room temperature. Modified monomeric cinchona alkaloids bearing alkylacetate side chains, including QD-AD, QD-(+)-MN, QD-(−)-MN, QD-IP, QD-TB, QD-IB, and QD-EF show overall efficiency (activity plus selectivity) comparable or superior to $(DHQD)_2AQN$. However, it is important to remember that QD-AD, QD-(+)-MN, QD-(−)-MN can be prepared in reasonable yield and at a cost significantly less than (<0.5% based on Aldrich price for starting material) that of $(DHQD)_2AQN$. In addition, as described in more detail later, the QD-(−)-MN catalyst has been shown to be sufficiently stable toward acid to be readily recyclable in high yield using a simple extraction procedure. On the other hand, initial experiments indicate that QD-TB may be too acid-sensitive to be recycled via a similar extraction procedure.

The efficiency of a variety of modified monomeric cinchona alkaloids in trifluoroethanolysis reactions was examined. Summarized in FIG. 3 are the results of a comparison of the efficiency of various catalysts for trifluoroethanolysis of 2,3-dimethylsuccinic anhydride in $Et_2O$ at 0.02 M concentration at room temperature. The data indicate that QD-AD, QD-(+)-MN, and QD-(−)-MN have a higher efficiency than $(DHQD)_2AQN$ when trifluoroethanol is used for the asymmetric alcoholysis. Interestingly, the enantioselectivity demonstrated by these three catalysts in combination with trifluoroethanol is equal to or better than that demonstrated by the combination of $(DHQD)_2AQN$ and methanol.

In order to evaluate substrate scope, a study was conducted on the alcoholysis of 3-methyl glutaric anhydride. The results of the alcoholysis of 3-methyl-glutaric anhydride at 0.02 and 0.2 M is summarized in FIGS. 4 and 5, respectively. 3-Substituted glutaric anhydrides are among the most readily accessible cyclic anhydrides. The corresponding ring opening products, 3-substituted hemiesters, are among the most useful chiral building blocks in organic synthesis. However, this class of anhydrides are the most challenging for alcoholysis due to low activity and more severe product inhibition of the catalysts. While $(DHQD)_2AQN$-catalyzed methanolysis of prochiral glutaric anhydrides afforded the hemiester in greater than 90% ee, the reaction has to be performed with high loading of catalyst (30 mol %) at low concentration (0.02 M); moreover, the transformation does not go to completion, rendering the procedure difficult to apply on a large scale. It is therefore highly significant that QD-AD can catalyze alcoholytic ring opening of glutaric anhydrides at relatively high concentration (0.2 M) providing the hemiester in high ee. Although the catalyst loading is 100-110 mol %, this procedure remains practical given than QD-AD can be prepared from inexpensive starting material and it can be recycled efficiently. Notably, unmodified quinidine is ineffective in transformations using 3-substituted glutaric anhydrides.

In order to evaluate the effect of solvent, a study was conducted in which toluene was used as the solvent. Displayed in FIG. 6 are the results of the methanolysis of 3-methyl gluratic anhydride in toluene at 0.2 M with different catalysts. Compared with $(DHQD)_2AQN$ under these conditions, QD-AD and QD-MN showed comparable enantioselectivity and slightly lower activity. On the other hand, QD-PP demonstrated significantly lower enantioselectivity and activity. QD-AD and QD-MN are clearly superior in consideration of both the cost and catalytic properties of these catalysts.

Shown in FIG. 7 are the results of the trifluoroethanolysis of 3-methyl gluratic anhydride in toluene at 0.2 M with various catalysts. Compared with either $(DHQD)_2AQN$ or QD-PP under these conditions, QD-AD and QD-MN showed better enantioselectivity and activity. The efficiency demonstrated by the combination of QD-(−)-MN with trifluoroethanol matched that by the combination of $(DHQD)_2AQN$ with methanol. Again, considering both the cost and catalytic properties, QD-AD and QD-MN are clearly superior to the dimeric catalysts.

Summarized in FIG. 8 are results on the methanolysis of 3-phenyl glutaric anhydride in toluene at 0.2 M with different catalysts. The results indicate that QD-AD and QD-(−)-MN are effective for 3-alkyl glutaric anhydrides and 3-aryl glutaric anhydrides. Compared with $(DHQD)_2AQN$ under these conditions, QD-AD and QD-MN showed slightly lower enantioselectivity and slightly lower activity. On the other hand, the QD-PP demonstrated significantly lower enantioselectivity and activity. Considering both the cost and catalytic properties, QD-AD and QD-MN are superior to the dimeric catalysts.

Summarized in FIG. 9 are results on the trifluoroethanolysis of 3-phenyl glutaric anhydride in toluene at 0.2 M with different catalysts. Compared with either $(DHQD)_2AQN$ or QD-PP under these conditions, QD-AD and QD-MN showed better enantioselectivity and activity. The efficiency demonstrated by the combination of QD-(−)-MN with trifluoroethanol matched that by the combination of $(DHQD)_2AQN$ with methanol. Again, considering both the cost and catalytic properties, QD-AD and QD-MN are superior to the dimeric catalysts.

Summarized in FIG. 10 are results on the methanolysis of 3-isopropyl glutaric anhydride in toluene at 0.2 M with different catalysts. First of all the results here indicate that QD-AD and QD-(−)-MN is effective for 3-alkyl glutaric anhydrides bearing branched substituent. Compared with $(DHQD)_2AQN$ under these conditions, QD-AD and QD-MN showed similar enantioselectivity and activity. On the other hand, the QD-PP demonstrated significantly lower enantioselectivity and activity. Consider both the cost and catalytic properties, QD-AD and QD-MN are clearly superior to the dimeric catalysts.

Summarized in FIG. 11 are results on the trifluoroethanolysis of 3-isopropyl gluratic anhydride in toluene at 0.2 M with different catalysts. Compared with either $(DHQD)_2AQN$ or QD-PP under these conditions, QD-AD and QD-MN showed better enantioselectivity and activity. The efficiency demonstrated by the combination of QD-(−)-MN with trifluoroethanol matched that of the combination of (DHQD)$_2$AQN with methanol. Again, considering both the cost and catalytic properties, QD-AD and especially QD-MN are clearly superior to the dimeric catalysts.

Summarized in FIG. 12 are results on the methanolysis of 3-OTBS gluratic anhydride in toluene at 0.2 M with different catalysts. Compared with either (DHQD)$_2$AQN under these conditions, QD-AD and QD-MN showed similar enantioselectivity and slightly lower activity. On the other hand, QD-PP demonstrated significantly inferior catalyst properties. Again, considering both the cost and catalytic properties, QD-AD and especially QD-MN are clearly superior to the dimeric catalysts.

Summarized in FIG. 13 are results on the trifluoroethanolysis of 3-OTBS gluratic anhydride in toluene at 0.2 M with different catalysts. Compared with either (DHQD)$_2$AQN or QD-PP under these conditions, QD-AD and QD-MN showed better enantioselectivity and activity. Again, considering both the cost and catalytic properties, QD-AD and especially QD-MN are clearly superior to the dimeric catalysts.

Summarized in FIGS. 14 and 15 are results on the methanolysis and trifluoroethanolysis of 3-substituted glutaric anhydrides with monomeric catalysts (Q-AD) derived from quinine. The products are the antipodes of those obtained with monomeric catalysts derived from quinidine.

In order to further evaluate the range of substrates amenable to this procedure, alcoholysis of 1,2,3,6-tetrahydrophthalic anhydrides was examined. The results on the methanolysis and trifluoroethanolysis of cis-1,2,3,6-tetrahydrophthalic anhydrides, a succinic anhydride, are summarized in FIGS. 16 and 17. With methanol as the nucleophile, QD-AD is comparable with (DHQD)$_2$AQN in terms of activity and selectivity. With trifluoroethanol as the nucleophile, QD-AD and QD-MN demonstrate better activity than and comparable selectivity to those demonstrated by (DHQD)$_2$AQN. However, the selectivity of QD-PP is slightly worse.

The results of the alcoholysis of a variety of structurally unique anhydrides is shown in FIGS. 18-25. Summarized in FIGS. 18 and 19 are results on the methanolysis and tricyclic succinic anhydrides. QD-AD and QD-MN demonstrate better activity and selectivity than those demonstrated by (DHQD)$_2$AQN and QD-PP. Summarized in FIGS. 20 and 21 are results on the methanolysis and trifluoroethanolysis of cis-1,2-cyclohexanedicarboxylic anhydrides. With trifluoroethanol as the nucleophile, QD-AD and QD-MN demonstrate comparable activity and selectivity to those demonstrated by (DHQD)$_2$AQN and better catalyst properties than that of QD-PP. Summarized in FIGS. 22 and 23 are results on the trifluoroethanolysis of cis-1,2-cyclohexanedicarboxylic anhydrides at 0.2 M in toluene and ether, respectively. In toluene, the amount of the alcohol used impacts the enantioselectivity of the reaction. Summarized in FIG. 24 are results on the trifluoroethanolysis of cis-1,2-cyclohexanedicarboxylic anhydrides at 0.5 M in toluene. The use of molecular sieves was beneficial for the reaction. Summarized in FIG. 25 are results on the alcoholysis of various succinic anhydrides with Q-AD.

Exemplification

The invention now being generally described, it will be more readily understood by reference to the following examples which are included merely for purposes of illustration of certain aspects and embodiments of the present invention, and are not intended to limit the invention.

EXAMPLE 1

Preparation of adamantyl chloroacetate (2)

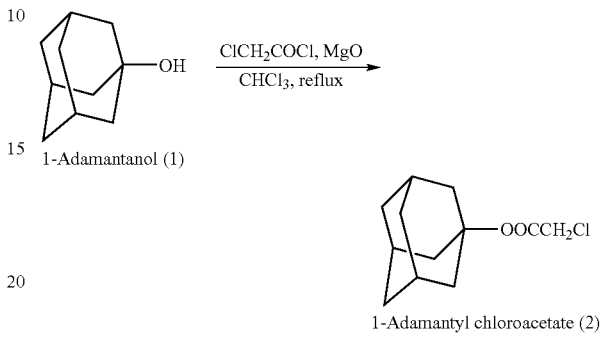

At 10° C. and under N$_2$, chloroacetyl chloride (9 mL, 113 mmol) was added slowly to a suspension of 1-adamantanol (11.4 g, 75 mmol) and MgO (4.5 g, 113 mmol) in CHCl$_3$ (150 mmol). The mixture was heated to slight reflux for 43 h and cooled to RT. The insoluble material was removed by filtration and the solvent was evaporated. The residue was crystallized in hexanes to afford 2 as a white solid (6.324 g, 37%). U.S. Pat. No. 4,456,611; Helv. Chim. Acta 1988, 71, 1553.

EXAMPLE 2

Preparation of (−)-menthyl chloroacetate (4a)

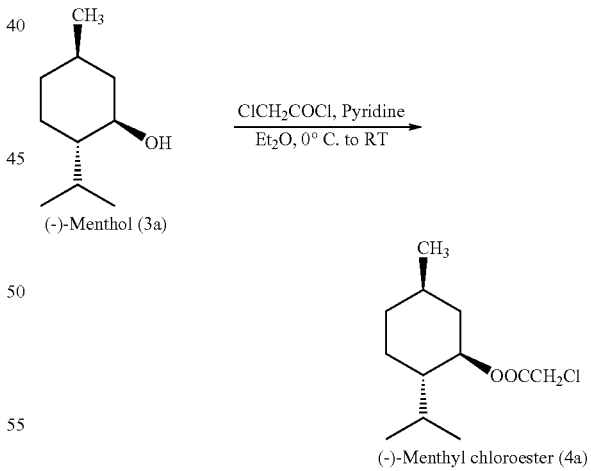

A solution of chloroacetyl chloride (6.4 mL, 80 mmol) in 40 mL anhydrous diethyl ether was added dropwise within 2 h to a solution of (−)-menthol (3a) (12.5 g, 80 mmol) and pyridine (6.5 mL, 80 mmol) in anhydrous diethyl ether (160 mL) at 0° C. After warming to RT, the white suspension was stirred for 2 h and the resulting mixture was then filtered. The filtrate was washed with HCl (60 mL, 2 N), saturated. NaHCO$_3$ (60 mL), brine and dried with Na$_2$SO$_4$. Removal of the solvent and drying under vacuum afford (−)-menthyl chloroacetate (4a) (17.64 g, 94%), which was used without further purification. U.S. Pat. No. 4,456,611; Helv. Chim. Acta 1988, 71, 1553.

EXAMPLE 3

Preparation of (+)-menthyl chloroacetate (4b)

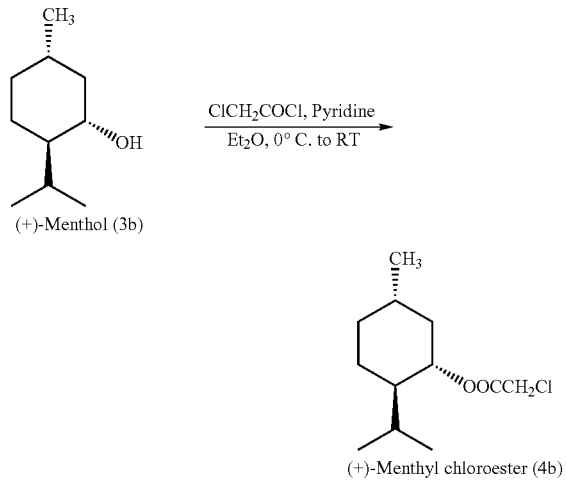

The procedure described in the preceding Example was carried out on 40 mmol scale to synthesis (+)-menthyl chloroester (4b) in 95% yield from (+)-menthol (3b). U.S. Pat. No. 4,456,611; Helv. Chim. Acta 1988, 71, 1553.

EXAMPLE 4

Synthesis of Chloroacetate Ester 5

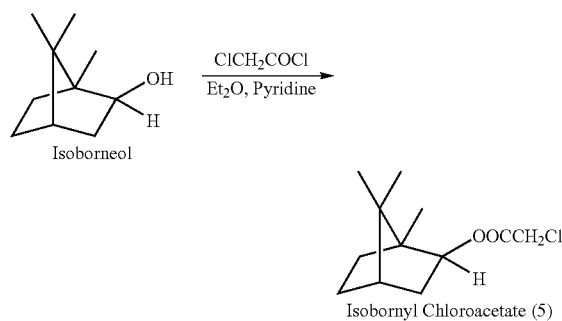

To a solution of isoborneol (9.255 g, 0.06 mol), pyridine (4.9 mL, 0.06 mol) in anhydrous diethyl ether (120 mL) at 0° C., chloroacetyl chloride (4.78 mL, 0.06 mol) in anhydrous diethyl ether (30 mL) was added dropwise during a period of 2 h. Then the reaction mixture was allowed to warm to room temperature and stirred for another 3 h. The resulting mixture was filtrated with the aid of Celite, washed with diethyl ether (30 mL). The combined organic layer was washed with aqueous HCl (2 N, 45 mL), followed by saturated aqueous NaHCO$_3$ (45 mL), then saturated brine (45 mL), dried over Na$_2$SO$_4$, concentrated to give yellow greenish oil (13.10 g, 95% yield) in NMR-pure form and was used without further purification.

EXAMPLE 5

Synthesis of (1R, 2R, 3R, 5S)-(−)-Isopinocamphyl chloroacetate (6)

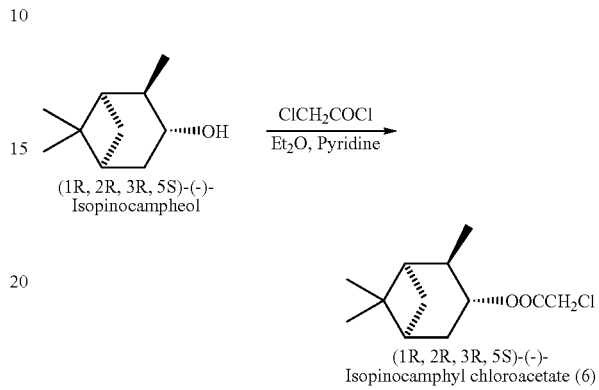

To a solution of (1R, 2R, 3R, 5S)-(−)-Isopinocampheol (9.255 g, 0.06 mol), pyridine (4.9 mL, 0.06 mol) in anhydrous diethyl ether (120 mL) at 0° C., chloroacetyl chloride (4.78 mL, 0.06 mol) in anhydrous diethyl ether (30 mL) was added dropwise during a period of 2 h. Then the reaction mixture was allowed to warm to room temperature and stirred for another 3 h. The resulting mixture was filtrated with the aid of Celite, washed with diethyl ether (30 mL). The combined organic layer was washed with aqueous HCl (2 N, 45 mL), followed by saturated aqueous NaHCO$_3$ (45 mL), then saturated brine (45 mL), dried over Na$_2$SO$_4$, concentrated to give yellow greenish oil (13.13 g, 95% yield) in NMR-pure form and was used without further purification.

EXAMPLE 6

Synthesis of (1R)-Endo-(+)-Fenchyl Chloroacetate (QD-EF, 7)

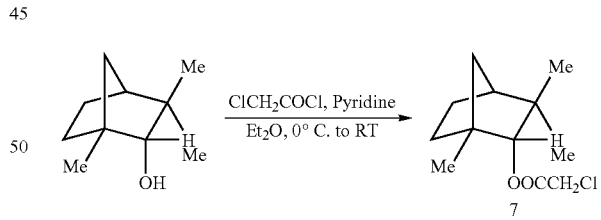

A solution of chloroacetyl chloride (6.4 mL, 80 mmol) in 40 mL anhydrous diethyl ether was added dropwise within 2 h to a solution of (1R)-Endo-(+)-Fenchyl Alcohol (12.25 g, 79.5 mmol) and pyridine (6.5 mL, 80 mmol) in 160 mL of anhydrous diethyl ether at 0° C. After warming to RT, the white suspension was stirred for 2.5 h. The precipitate was removed by filtration and washed by diethyl ether (30 mL). The combined organic solution was washed with HCl (2 N, 60 mL), followed by sat. NaHCO3 (60 mL), sat. NaCl (60 mL) solutions and dried with Na$_2$SO$_4$. Removal of the solvent and drying at vacuum afford (1R)-Endo-(+)-Fenchyl Chloroacetate (17.33 g, 94.5%) which was used without further purification.

EXAMPLE 7

Synthesis of O-[(−)-menthylacetate)]quinidine and O-[(+)-menthylacetate]quinidine (QD-(−)-MN)

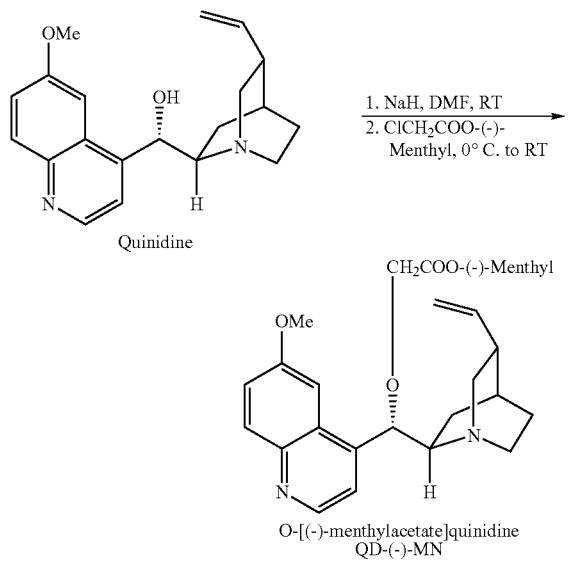

Procedure A (Using Chromatography Purification)

Under a nitrogen atmosphere, NaH (60 mg, 1.5 mmol, 60% in mineral oil) was washed with hexanes (2×3 mL) and suspended in DMF (5 mL). Quinidine (0.324 g, 1.0 mmol) was added to the mixture in small portions. The reaction mixture was stirred until the solution turned a yellow color (about 3 h). It was then cooled to 0° C. (−)-Menthyl chloroacetate (4a) (0.349 g, 1.5 mmol) was added dropwise over one minute to the cooled reaction mixture. The reaction mixture was stirred for 0.5 h at 0° C., then warmed to room temperature and kept at that temperature for 1.5 h. It is then carefully quenched with $H_2O$ (10 mL) the mixture is mixed with ethyl acetate (15 mL). The organic and aqueous layers were separated. The aqueous phase was extracted with ethyl acetate (15 mL). The organic phases were combined, washed with sat. $NaHCO_3$ (10 mL), water (3×10 mL), brine (10 mL), dried over $Na_2SO_4$, and concentrated under reduced pressure. The brown residue was purified by flash chromatography (ethyl acetate:methanol=10:1) to afford O-((−)-menthylacetate)quinidine (0.2752 g, 53%) as a white foam.

1H NMR ($CDCl_3$): δ 6 0.73 (d, J=6.8 Hz, 3H), 0.76-1.10 (m, 9H), 1.22-1.40 (m, 2H), 1.40-1.60 (m, 3H), 1.60-1.72 (m, 2H), 1.72-1.84 (m, 2H), 1.93-2.20 (m, 1H), 2.14-2.32 (m, 2H), 2.70-2.90 (m, 3H), 3.04-3.16 (m, 1H), 3.28-3.44 (br, 1H), 3.89 (d, J=16.4 Hz, 1H), 3.93 (s, 3H), 4.06 (d, J=16.0 Hz, 1H), 4.77 (td, J=11.2, 4.4, 1H), 5.08-5.15 (m, 2H), 5.20-5.45 (br, 1H), 6.12-6.21 (m, 1H), 7.20-7.50 (m, 3H), 8.04 (d, J=8.8 Hz, 1H), 8.76 (d, J=4.4 Hz, 1H).

Synthesis of O-((+)-menthylacetate)quinidine (QD-(+)-MN)

The procedure described above was used to prepare O-[(+)-menthylacetate]quinidine as a white foam in 43% yield. 1H NMR ($CDCl_3$): 0.75 (d, J=7.2 Hz, 3H), 0.85 (d, J=7.6 Hz, 3H), 0.90 (d, J=6.8 Hz, 3H), 0.78-1.12 (m, 3H), 1.20-1.40 (m, 2H), 1.42-1.94 (m, 7H), 1.97-2.06 (m, 1H), 2.26-2.48 (m, 2H), 2.80-3.30 (m, 4H), 3.46-3.90 (br, 1H), 3.99 (d, J=16 Hz, 1H), 4.00 (s, 3H), 4.08 (d, J=16.0 Hz, 1H), 4.79 (td, J=10.8, 4.8, 1H), 5.10-5.30 (m, 2H), 5.46-6.10 (br, 1H), 6.10-6.24 (m, 1H), 7.36-7.56 (m, 3H), 8.04 (d, J=9.2 Hz, 1H), 8.76 (d, J=4.4 Hz, 1H).

Procedure B (Purification Without Chromatographic Separation) for Preparation of QD-(−)-MN Under a nitrogen atmosphere, NaH (0.52 g, 12.9 mmol, 60% in mineral oil) was washed with hexanes (2×9 mL) and suspended in DMF (43 mL). Quinidine (2.786 g, 8.6 mmol) was added to the mixture in small portions. The reaction mixture was stirred until the solution turned a yellow color (about 2.5 h). It was then cooled to 0° C. (−)-menthyl chloroacetate (3.0 g, 12.9 mmol) was added dropwise over a 1 min period to the cooled reaction mixture. The reaction mixture was stirred for 1 h at 0° C., 1.5 h at RT. The mixture was cooled to 0° C. again, carefully quenched with $H_2O$ (60 mL) and then ethyl acetate (60 mL) was added. The organic and aqueous layers were separated. The aqueous phase was extracted with ethyl acetate (30 mL). The organic phases were combined, washed with sat. $NaHCO_3$ (30 mL), water (3×30 mL), sat. NaCl (30 mL), and then extracted by 3×40 mL 5% w/w HCl. The combined acidic aqueous phase was extracted by 2×50 mL $CH_2Cl_2$. The combined organic phase was washed by 25 mL 5% w/w HCl and concentrated under reduced pressure. The brown residue was dissolved in 100 mL 0.1 N HCl. The aqueous phase was extracted by 50 mL $Et_2O$ to remove trace impurities, basified to pH=11 by KOH and extracted by 2×50 mL ether. The combined organic phase was dried over $Na_2SO_4$ and concentrated under reduced pressure to afford crude O-((−)-menthylacetate)quinidine as a yellowish foam. This crude produce was dissolved in 40 mL of anhydrous diethyl ether and treated dropwise with 0.95 equiv of 1.0 M solution of hydrogen chloride in diethyl ether (Aldrich) to precipitate the O-((−)-menthylacetate)quinidine hydrochloride. The seperated precipitate was washed by 2×10 mL diethyl ether, dried in air and suspended in 50 mL $H_2O$. KOH was used to adjusted the solution's pH=11 and the resulted mixture was extracted by 3×50 mL diethyl ether. The combined organic phase was dried with $Na_2SO_4$ and concentrated under reduced pressure to afford O-((−)-menthylacetate)quinidine (1.783 g, 40%) as an off white crystalline foam.

EXAMPLE 8

Synthesis of O-(1-adamantylacetate)quinidine (QD-AD)

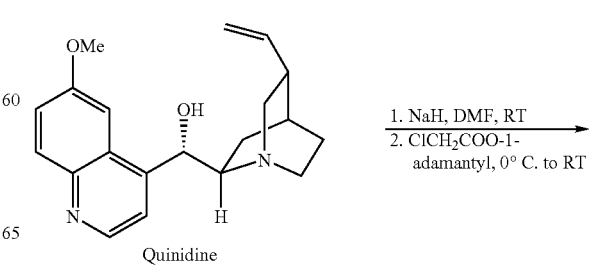

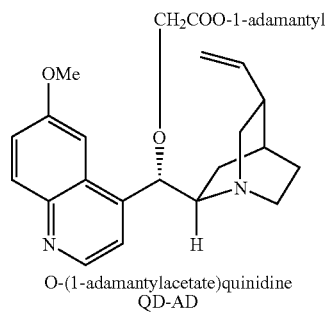

O-(1-adamantylacetate)quinidine
QD-AD

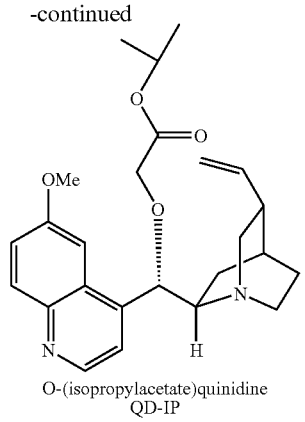

O-(isopropylacetate)quinidine
QD-IP

Under a nitrogen atmosphere, NaH (80 mg, 2 mmol, 60% in mineral oil) was washed with hexanes (2×3 mL) and suspended in DMF (3 mL). Quinidine (0.1944 g, 0.6 mmol) was added to the mixture in small portions. The reaction mixture was stirred until the solution turned a yellow color (about 2 h). It was then cooled to 0° C. 1-Adamantyl chloroacetate (0.2285 g, 1 mmol) was added in small portions to the cooled reaction mixture. The reaction mixture was stirred for 3 h at RT, cooled to 0° C., carefully quenched with $H_2O$ (5 mL) and then was extracted with toluene (4×10 mL). The organic phases were combined, washed with water (5×5 mL), dried over $Na_2SO_4$, and concentrated under reduced pressure. The brown residue was purified by flash chromatography (ethyl acetate:methanol=9:1) to afford O-(1-adamantylacetate)quinidine (0.1640 g, 53%) as a white foam. 1H NMR ($CDCl_3$): δ 1.22-1.38 (m, 1H), 1.44-1.59 (m, 2H), 1.59-1.69 (m, 6H), 1.74-1.80 (m, 1H), 2.04-2.12 (m, 6H), 2.12-2.18 (m, 3H), 2.18-2.31 (m, 2H), 2.70-3.15 (m, 4H), 2.30-3.48 (m, 1H), 3.78 (d, J=16 Hz, 1H), 3.94 (s, 3H), 3.95 (d, J=16 Hz, 1H), 5.08-5.15 (m, 2H), 5.20-5.50 (br, 1H), 6.11-6.22 (m, 1H), 7.27-7.50 (m, 3H), 8.04 (d, J=9.2 Hz, 1H), 8.76 (d, J=4 Hz, 1H).

EXAMPLE 9

Synthesis of O-(isopropylacetate)guinidine (QD-IP)

Under a nitrogen atmosphere, NaH (160 mg, 4 mmol, 60% in mineral oil) was washed with hexanes (2×5 mL) and suspended in DMF (15 mL). Quinidine (0.972 g, 3 mmol) was added to the mixture in small portions. The reaction mixture was stirred until the solution turned a yellow color (about 2 h). It was then cooled to 0° C. Isopropyl chloroacetate (0.683 g, 5 mmol) was added in one portion to the cooled reaction mixture. The reaction mixture was stirred for 3 h at 0° C., 25 h at RT. Then another portion of Isopropyl chloroacetate (0.342 g, 2.5 mmol) was added in one portion. The mixture was stirred at RT for 13 h and carefully quenched with $H_2O$ (20 mL) and then toluene (20 mL) was added. The organic and aqueous layers were separated. The aqueous phase was extracted with toluene (3×10 mL). The organic phases were combined, washed with water (5×10 mL), dried over $Na_2SO_4$, and concentrated under reduced pressure. The brown residue was purified by flash chromatography (ethyl acetate:methanol=10:1) to afford O-(isopropylacetate)quinidine (0.1884 g, 15%) as a light yellow oil. 1H NMR ($CDCl_3$): δ 1.23 (d, J=6.0 Hz, 6H), 1.20-1.38 (m, 1H), 1.42-1.60 (m, 2H), 1.75-1.84 (m, 1H), 2.16-2.32 (m, 2H), 2.71-3.02 (m, 3H), 3.05-3.18 (m, 1H), 3.30-3.50 (m, 1H), 3.86 (d, J=16.8 Hz, 1H), 3.94 (s, 3H), 4.04 (d, J=16.4 Hz, 1H), 5.02-5.20 (m, 3H), 5.26-5.44 (br, 1H), 6.11-6.24 (m, 1H), 7.24-7.54 (m, 3H), 8.04 (d, J=9.2 Hz, 1H), 8.76 (d, J=4.4 Hz, 1H).

EXAMPLE 10

Synthesis of isobomyl quinidine and (1R, 2R, 3R, 5S)-(−)-isopinocamphyl quinidine (QD-IB)

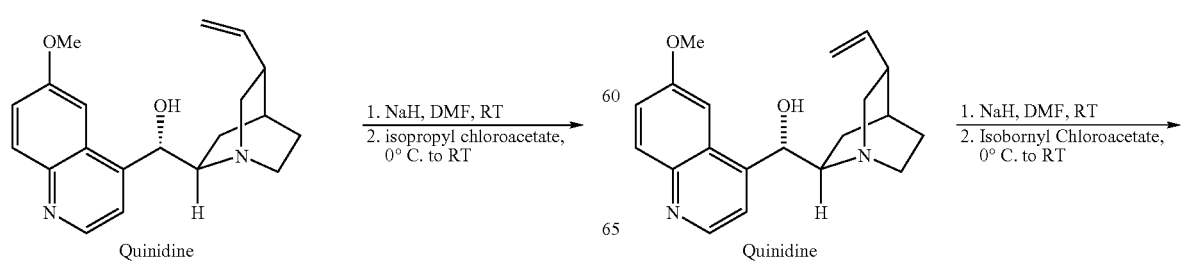

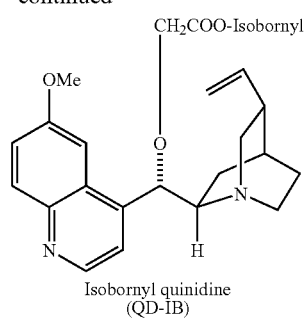

Isobornyl quinidine
(QD-IB)

Under a nitrogen atmosphere, NaH (300 mg, 7.5 mmol, 60% in mineral oil) was washed with hexanes (2×5 mL) and suspended in DMF (25 mL). Quinidine (1.62 g, 5.0 mmol) was added to the mixture in small portions. The reaction mixture was stirred until the solution turned a yellow color (about 2 h). It was then cooled to 0° C. Isobornyl chloroacetate (1.728 g, 7.5 mmol) was added dropwise over a 2 min period to the cooled reaction mixture. The reaction mixture was stirred for 1 h at 0° C., 1 h at RT, and carefully quenched with H$_2$O (35 mL) and then ethyl acetate (35 mL) was added. The organic and aqueous layers were separated. The aqueous phase was extracted with ethyl acetate (35 mL). The organic phases were combined, washed with sat. NaHCO$_3$ (17 mL), water (3×17 mL), sat. NaCl (17 mL), dried over Na$_2$SO$_4$, and concentrated under reduced pressure. The brown residue was purified by flash chromatography (ethyl acetate:methanol=20:1 ) to afford isobornylacetate)quinidine (1.218 g, 47%) as a white foam.

EXAMPLE 11

Synthesis of (1R, 2R, 3R, 5S)-(–)-isopinocamphyl quinidine [QD-(–)-IPC]

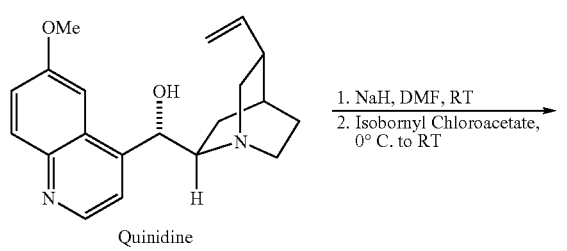

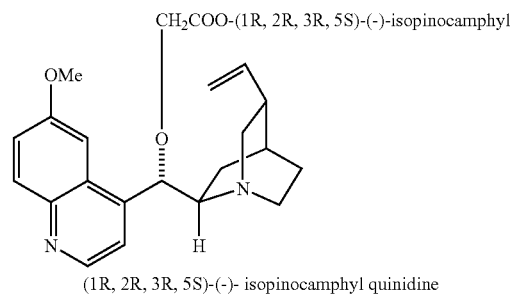

(1R, 2R, 3R, 5S)-(–)- isopinocamphyl quinidine

The procedure described in the preceding Example afforded (1R, 2R, 3R, 5S)-(–)-isopinocamphyl chloroacetate) quinidine (QD-(–)-IPC) as a white foam in 45% yield.

EXAMPLE 12

Synthesis of O-((1R)-Endo-(+) Fenchylacetate)quinidine

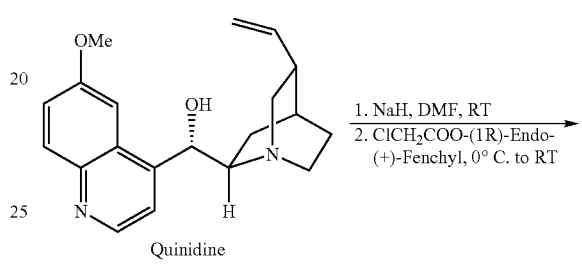

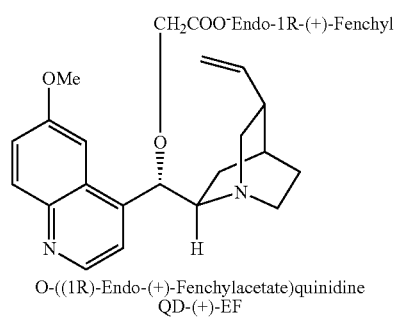

O-((1R)-Endo-(+)-Fenchylacetate)quinidine
QD-(+)-EF

Under a nitrogen atmosphere, NaH (0.3 g, 7.5 mmol, 60% in mineral oil) was washed with hexanes (2×5 mL) and suspended in DMF (25 mL). Quinidine (1.620 g, 5 mmol) was added to the mixture in small portions. The reaction mixture was stirred until the solution turned a yellow color (about 2.5 h). It was then cooled to 0° C. (1R)-Endo-(+)-Fenchyl Chloroacetate (1.728 g, 7.5 mmol) was added dropwise over a 1 min period to the cooled reaction mixture. The reaction mixture was stirred for 1 h at 0° C., 1.5 h at RT, and carefully quenched with H$_2$O (35 mL) and then ethyl acetate (35 mL) was added. The organic and aqueous layers were separated. The aqueous phase was extracted with ethyl acetate (35 mL). The organic phases were combined, washed with sat. NaHCO$_3$ (17 mL), water (3×17 mL), sat. NaCl (17 mL), dried over Na$_2$SO$_4$, and concentrated under reduced pressure. The brown residue was purified by flash chromatography (ethyl acetate:methanol=9:1) to afford O-((1R)-Endo-(+)-Fenchylacetate)quinidine (1.0119 g, 39%) as a light yellowish foam.

EXAMPLE 13

Synthesis of O-cyanomethylquinidine (QD-CN)

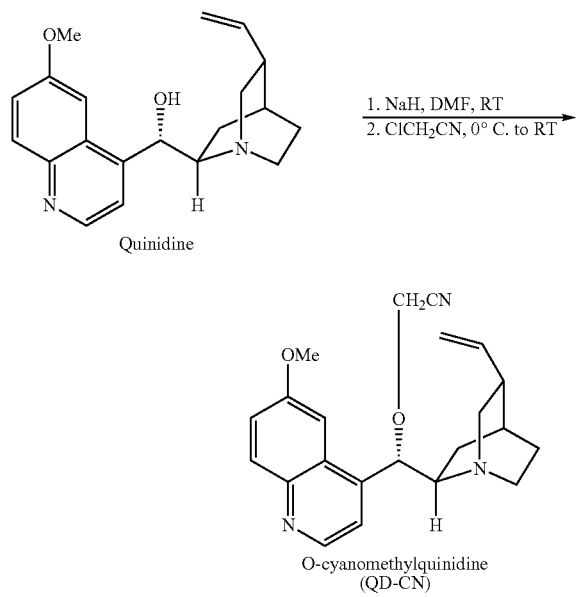

Under a nitrogen atmosphere, NaH (0.266 g, 6.66 mmol, 60% in mineral oil) was washed with hexanes (2×10 mL) and suspended in DMF (10 mL). Quinidine (0.648 g, 2 mmol) was added to the mixture in small portions. The reaction mixture was stirred until the solution turned a yellow color (about 2 h). It was then cooled to 0° C. Chloroacetonitrile (0.227 g, 3 mmol) was added dropwise over a 5 min period to the cooled reaction mixture. The reaction mixture was stirred for 1.5 h at 0° C. and then 1.5 h at room temperature (TLC check, conversion 40%, ethyl acetate:methanol=5:2). The mixture was again cooled to 0° C., chloroacetonitrile (0.227 g, 3 mmol) was added dropwise over a 5 min period and the reaction mixture was allowed to stir overnight at room temperature (TLC check, no enhancement of conversion, ethyl acetate:methanol=5:2). The mixture was cooled to 0° C. and carefully quenched with $H_2O$ (13 mL) and then toluene (13 mL) was added. The organic and aqueous layers were separated. The aqueous phase was extracted with toluene (3×7 mL). The organic phases were combined, washed with sat. $NaHCO_3$ (7 mL), sat. NaCl (7 mL), water (5×7 mL), dried over $Na_2SO_4$, and concentrated under reduced pressure. The black residue was purified by flash chromatography (ethyl acetate:methanol=5:2) to afford O-cyanomethylquinidine (85.4 mg, 12%) as a light brown viscous oil.

1H NMR ($CDCl_3$): 1.32-1.88 (m, 4H), 1.95-2.10 (m, 1H), 2.25-2.36 (m, 1H), 2.70-2.89 (m, 2H), 2.91-3.03 (m, 1H), 3.05-3.22 (m, 2H), 3.97 (s, 3H), 4.03 (d, J=16.0 Hz, 1H), 4.31 (d, J=16.0 Hz, 1H), 5.09-5.18 (m, 2H), 5.33-5.56 (br, 1H), 5.99-6.11 (m, 1H), 7.30-7.46 (m, 3H), 8.05 (d, J=9.2 Hz, 1H), 8.77 (d, J=4.8 Hz, 1H).

EXAMPLE 14

Synthesis of O-(1-pinacolone)quinidine (QD-PC)

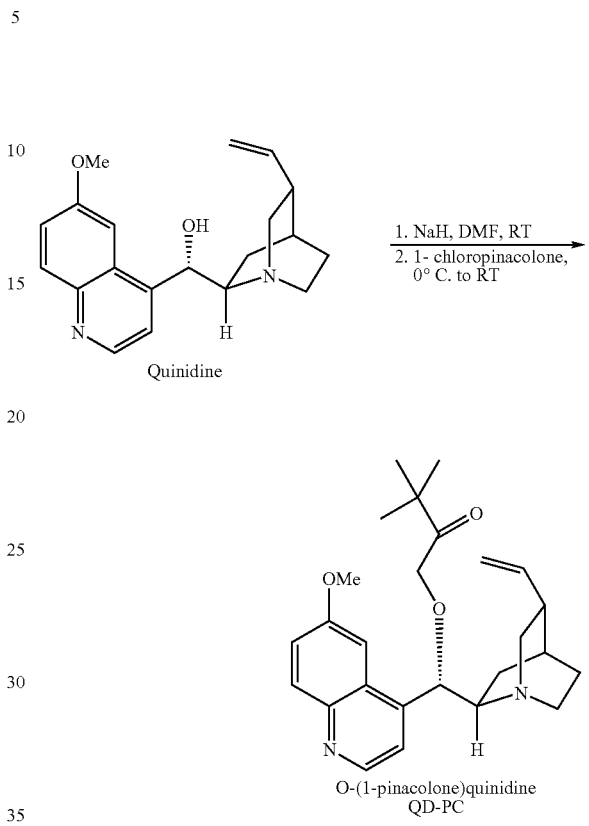

Under a nitrogen atmosphere, NaH (160 mg, 4 mmol, 60% in mineral oil) was washed with hexanes (2×5 mL) and suspended in DMF (15 mL). Quinidine (0.972 g, 3 mmol) was added to the mixture in small portions. The reaction mixture was stirred until the solution turned a yellow color (about 2 h). It was then cooled to 0° C. 1-chloropinacolone (0.670 g, 5 mmol) was added in one portion to the cooled reaction mixture. The reaction mixture was stirred for 0.5 h at 0° C., 3.5 h at RT. Then another portion of 1-chloropinacolone (0.670 g, 5 mmol) was added in one portion. The mixture was stirred at RT for 36 h and carefully quenched with $H_2O$ (20 mL) and then toluene (20 mL) was added. The organic and aqueous layers were separated. The aqueous phase was extracted with toluene (2×20 mL). The organic phases were combined, washed with water (5×10 mL), dried over $Na_2SO_4$, and concentrated under reduced pressure. The brown residue was purified by flash chromatography (ethyl acetate:methanol=5:1) to afford O-(1-pinacolone)quinidine (0.3296 g, 26%) as a colorless oil. 1H NMR ($CDCl_3$): δ 1.06 (s, 9H), 1.23-1.38 (m, 1H), 1.45-1.63 (m, 2H), 1.76-1.84 (m, 1H), 2.22-2.38 (m, 2H), 2.72-3.20 (m, 4H), 3.32-3.54 (m, 1H), 3.95 (s, 3H), 4.20 (d, J=18.0 Hz, 1H), 4.29 (d, J=17.2 Hz, 1H), 5.10-5.20 (m, 2H), 5.26-5.48 (m, 1H), 6.16-6.26 (m, 1H), 7.30-7.48 (m, 3H), 8.04 (d, J=9.2 Hz, 1H), 8.75 (d, J=4.4 Hz, 1H).

EXAMPLE 15

Synthesis of O-pivaloylquinidine (QD-Piv)

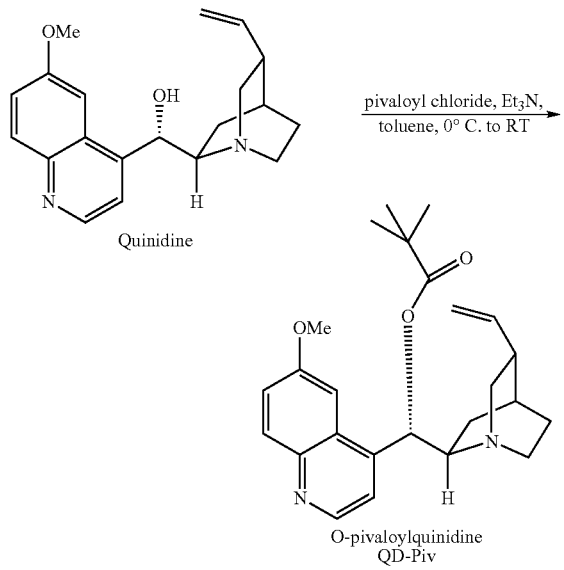

To a stirred suspension of Quinidine (0.972 g, 3 mmol) in toluene at 0° C., pivaloyl chloride (0.362 g, 3 mmol) was added dropwise, followed by adding triethyl amine (1 mL). The reaction mixture was stirred at RT for 9.5 h. Then another portion of pivaloyl chloride (0.362 g, 3 mmol) was added in one portion. The mixture was stirred at RT for 13 h and carefully quenched with $H_2O$ (20 mL) and then toluene (20 mL) was added. The organic and aqueous layers were separated. The aqueous phase was extracted with toluene (20 mL). The organic phases were combined, washed with sat. $NaHCO_3$ (10 mL), sat. NaCl (2×10 mL), dried over $Na_2SO_4$, and concentrated under reduced pressure. The brown residue was purified by flash chromatography (ethyl acetate:methanol=10:1 ) to afford O-pivaloylquinidine (0.5582 g, 46%) as a colorless oil. 1H NMR ($CDCl_3$): δ 1.22 (s, 9H), 1.48-1.66 (m, 3H), 1.74-1.86 (m, 2H), 2.30-2.52 (m, 1H), 2.65-2.82 (m, 2H), 2.92 (d, J=8.8 Hz, 2H), 3.26-3.38 (m, 1H), 3.96 (s, 3H), 5.06-5.15 (m, 2H), 5.97-6.08 (m, 1H), 6.44 (d, J=8.0 Hz, 1H), 7.31-7.45 (m, 3H), 8.00 (d, J=9.2 Hz, 1H). 8.73 (d, J=4.4 Hz, 1H).

EXAMPLE 16

Synthesis of O-(1-adamantylacetate)quinine (Q-AD)

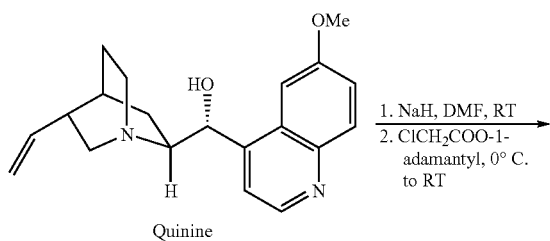

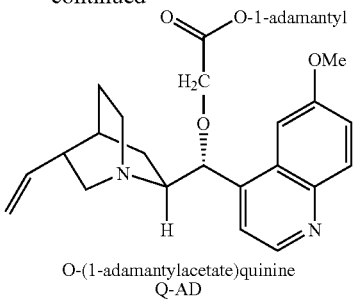

O-(1-adamantylacetate)quinine
Q-AD

Under a nitrogen atmosphere, NaH (180 mg, 4.5 mmol, 60% in mineral oil) was washed with hexanes (2×5 mL) and suspended in DMF (15 mL). Quinine (0.972 g, 3 mmol) was added to the mixture in small portions. The reaction mixture was stirred until the solution turned a yellow color (about 4.5 h). It was then cooled to 0° C. 1-adamantyl chloroacetate (1.028 g, 4.5 mmol) was added in small portions to the cooled reaction mixture. The reaction mixture was stirred for 1 h at 0° C., 1 h at RT, cooled to 0° C., carefully quenched with $H_2O$ (20 mL) and then was extracted with ethyl acetate (20 mL, 10 mL). The organic phases were combined, washed with sat. $NaHCO_3$ (10 mL), water (3×10 mL), sat. NaCl (10 mL), dried over $Na_2SO_4$, and concentrated under reduced pressure. The brown residue was purified by flash chromatography (ethyl acetate:methanol=10:1) to afford O-(1-adamantylacetate) quinine (0.4222 g, 27%) as a white foam. 1H NMR ($CDCl_3$): δ 1H NMR ($CDCl_3$): δ 1.48-1.76 (m, 8H), 1.78-2.01 (m, 3H), 2.04-2.12 (m, 6H), 2.12-2.20 (m, 3H), 2.24-2.39 (m, 1H), 2.56-2.80 (m, 2H), 3.03-3.27 (m, 2H), 3.44-3.72 (m, 1H), 3.76 (d, J=16 Hz, 1H), 3.96 (s, 3H), 3.97 (d, J=16 Hz, 1H), 4.90-5.01 (m, 2H), 5.20-5.56 (br, 1H), 5.70-5.80 (m, 1H), 7.30-7.50 (m, 3H), 8.04 (d, J=9.2 Hz, 1H), 8.76 (d, J=4.4 Hz, 1H).

EXAMPLE 17

General Procedure for the Alcoholysis of 2,3-dimethyl succinic Anhydride

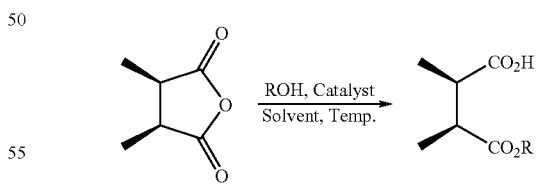

Alcohol (0.1-1.0 mmol) was added to a solution of anhydride (0.05-0.2 mmol) and catalyst (5-110 mol %) in solvent (0.5-5.0 mL) at the reaction temperature indicated in the table. The reaction mixture was initially stirred and then allowed to sit at that temperature until the starting material was consumed as indicated by TLC analysis* or Chiral GC (β-CD, 130° C./20 min)** analysis (0.5 h-37 d). The reaction was quenched by adding HCl (1 N, 5 mL) in one portion. The aqueous phase was extracted with ether (2×20 mL). The organic phase was combined, dried over $Na_2SO_4$, and concentrated to provide the desired product. The enantiomeric excess (ee) of the product was determined by HPLC analysis of a diastereoisomeric mixture of the corresponding amide-ester prepared from the product according to a modified literature procedure (for trifluoroethyl ester) or chiral GC analysis ($\beta$-CD, 130° C./20 min) (for methyl ester).

EXAMPLE 18

Preparation of amide-ester for ee Analysis with a Modified Literature Procedure (See J. Hiratake, M. Inagaki, Y Yamamoto, J. Oda, *J. Chem. Soc., Perkin Trans.* 1, 1987, 1053)

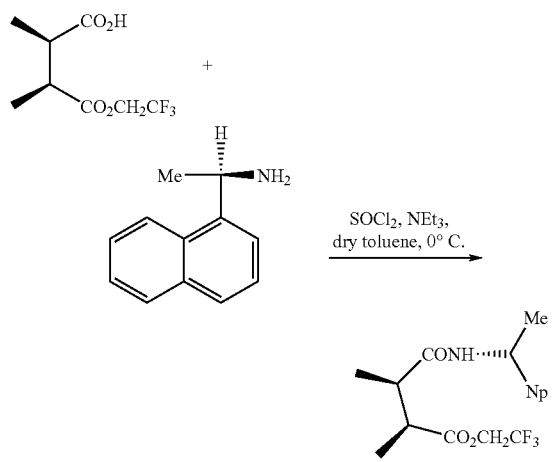

To a solution of hemiester (0.1 mmol) in dry toluene (3.0 mL) at 0° C. was added thionyl chloride (14.3 mg, 0.12 mmol). The mixture was allowed to stir at 0° C. for 10 min followed by the addition of (R)-1-(1-naphthyl)ethylamine (18.8 mg, 0.11 mmol) and triethylamine (33.4 mg, 0.33 mmol). The resulting mixture was allowed to stir for 30 minutes at 0° C. followed by another 30 minutes at room temperature. The reaction was then quenched with HCl (1 N, 5 mL), diluted with EtOAc (20 mL), and washed with saturated $NaHCO_3$ (5 mL) and brine (5 mL). The organic layer was dried with $Na_2SO_4$.

EXAMPLE 19

General Procedure for the Alcoholysis of Prochiral Cyclic Anhydrides

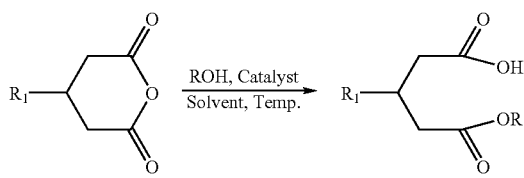

Alcohol (0.15-1.0 mmol) was added to a solution of anhydride (0.1 mmol) and catalyst (20-110 mol %) in solvent (0.5-5.0 mL) at the reaction temperature indicated in the table. The reaction mixture was stirred at that temperature until the starting material is consumed as indicated by GC ($\beta$-CD) analysis (19-141 h). The reaction was quenched by adding HCl (1 N, 4 mL) in one portion (when an acid-sensitive substrate, such as 3-tert-butyldimethylsilyl glutaric anhydride was used, $H_3PO_4$ (1.0 M) was used to quench the reaction). The aqueous phase was extracted with ether (40 mL). The organic phase was washed by another portion of HCl (1 N, 4 ml)*, dried over $Na_2SO_4$, and concentrated to provide the desired product with or without further purification by flash chromatography. The enantiomeric excess (ee) of each product was determined by HPLC analysis of a diastereoisomeric mixture of the corresponding amide-ester prepared from the hemiester according to a modified literature procedure or chiral GC analysis.

EXAMPLE 20

Preparation of Amide-Ester for ee Analysis (See J. Hiratake, M. Inagaki, Y. Yamamoto, J. Oda, *J. Chem. Soc., Perkin Trans.* 1, 1987, 1053)

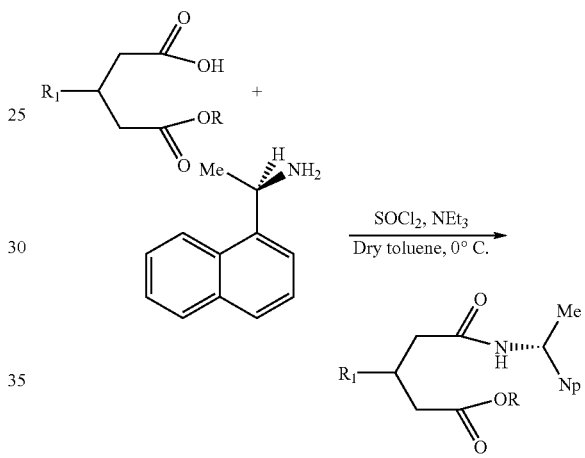

A mixture of the hemiester (0.1 mmol) and $SOCl_2$ (14.3 mg, 0.12 mmol) in toluene (3 mmol) was allowed to cool to 0° C. and kept at that temperature for 10 minutes. To the resulting solution, (R)-1-(1-naphthyl)ethyl-amine (18.8 mg, 0.11 mmol) and triethyl amine (33.4 mg, 0.33 mmol) were then added. The resulting mixture was allowed to stir for 30 minutes at 0° C. followed by another 30 minutes at room temperature. The reaction was then quenched with HCl (1 N, 5 mL), diluted with EtOAc (20 mL), and washed with saturated $NaHCO_3$ (5 mL) and brine (5 mL). The organic layer was dried with $Na_2SO_4$.

EXAMPLE 21

General Procedure for the Alcoholysis of Prochiral Cyclic Anhydrides

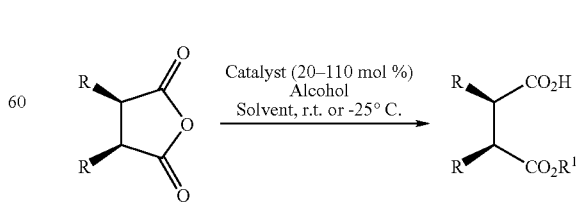

Alcohol (0.15-1.0 mmol) was added to a solution of anhydride (0.1 mmol) and catalyst (20-110 mol %) in the respective solvent (0.5-5.0 mL) at the reaction temperature indicated in the table. The reaction mixture was initially stirred and then allowed to sit at that temperature until the starting material is consumed as indicated by TLC analysis (2-186 h). The reaction was quenched by adding HCl (1 N, 3 mL) in one portion. The aqueous phase was extracted with ether (2×10 mL). The organic phase was combined, washed with HCl (1 N, 2×3 mL), dried over $Na_2SO_4$, and concentrated to provide the desired product without further purification. The product was determined pure as indicated by NMR. The enantiomeric excess (ee) of each product was determined by HPLC analysis of a diastereoisomeric mixture of the corresponding amide-ester prepared from the hemiester according to a modified literature procedure.

EXAMPLE 22

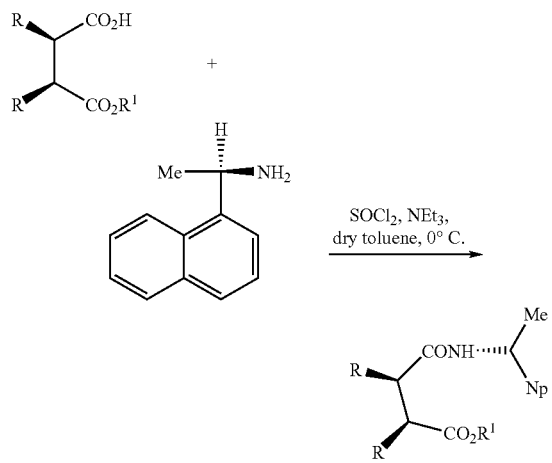

(See J. Hiratake, M. Inagaki, Y Yamamoto, J. Oda, *J. Chem. Soc., Perkin Trans.* 1, 1987, 1053)

To a solution of hemiester (0.1 mmol) in dry toluene (3 mL) at 0° C. was added thionyl chloride (14.3 mg, 0.12 mmol). The mixture was allowed to stir at 0° C. for 10 min followed by the addition of (R)-1-(1-naphthyl)ethylamine (18.8 mg, 0.11 mmol) and triethylamine (33.4 mg, 0.33 mmol), respectively. The resulting mixture was allowed to stir for 30 minutes at 0° C. followed by another 30 minutes at room temperature. The reaction was then diluted with EtOAc (20 mL) and washed successively with HCl (1 N, 10 mL), saturated $NaHCO_3$ (10 mL) and saturated brine (10 mL). The organic layer was dried with $Na_2SO_4$.

EXAMPLE 23

Procedure for trifluoroethanolysis of cis-1,3-Dibenzyl-tetrahydro-2H-furo[3,4-d]imidazole-2,4,6-trione

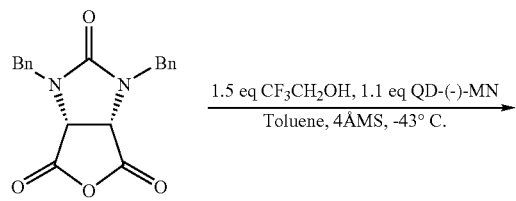

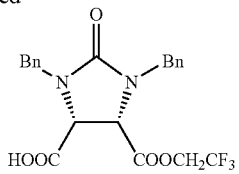

A mixture of QD-(−)-MN (57.2 mg, 0.11 mmol) and 4 Å molecular sieves (22 mg) in anhydrous toluene was stirred at RT for 5 minutes, then cis-1,3-Dibenzyl-tetrahydro-2H-furo[3,4-d]imidazole-2,4,6-trione (33.6 mg, 0.10 mmol) was added, after which the mixture was cooled to −43° C. and stirred for another 10 minutes. $CF_3CH_2OH$ was added in one portion. The mixture was stirred at that temperature until the starting material was consumed as indicated by TLC (20% methanol in methylene chloride) analysis (9 h). Aq. HCl (1.0 N, 4.0 mL) was added to quench the reaction. The aqueous phase was extracted by 40 mL diethyl ether. The combined organic phase was washed by another portion of aq. HCl (1 N, 4 mL), dried with $NaSO_4$ and concentrated to afford the hemiester as a white solid (38.8 mg, 89%, 94% ee) which is pure by NMR. The enantiomeric excess (ee) of the product was determined by HPLC analysis of a diastereoisomeric mixture of the corresponding amide-ester prepared from the hemiester according to a modified literature procedure.

EXAMPLE 24

Procedure for ee Analysis (See J. Hiratake, M. Inagaki, Y Yamamoto, J. Oda, *J. Chem. Soc., Perkin Trans.* 1, 1987, 1053)

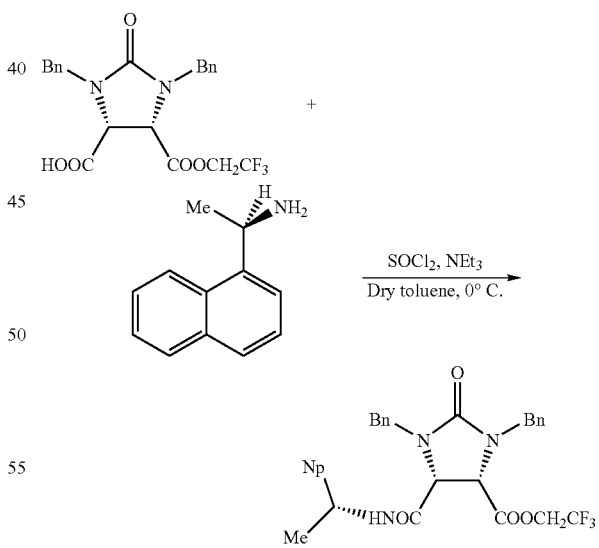

To a solution of hemiester (0.1 mmol) in dry toluene (6 mL) and methylene chloride (6 mL) at 0° C. was added thionyl chloride (14.3 mg, 0.12 mmol). The mixture was allowed to stir at 0° C. for 15 min followed by the addition of (R)-1-(1-naphthyl)ethylamine (18.8 mg, 0.11 mmol) and triethylamine (33.4 mg, 0.33 mmol), respectively. The resulting mixture was allowed to stir for 1 h at 0° C. followed by another 1 h at room temperature. The reaction was then quenched with HCl (1 N, 5 mL), diluted with EtOAc (40 mL), and washed with saturated NaHCO$_3$ (5 mL) and saturated brine (5 mL), respectively. The organic layer was dried with Na$_2$SO$_4$ and concentrated to half of its original volume.

EXAMPLE 25

Procedure for Alcoholysis of Cis-1,2,3,6-Tetrahydrophthalic Anhyride at 1.0 mmol Scale and Catalyst Recovery

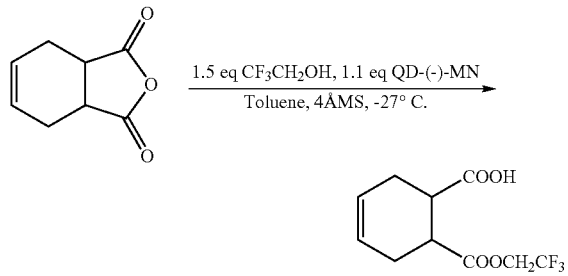

A mixture of QD-(−)-MN (purified by hydrochloride salt) (572 mg, 1.1 mmol) and 4 Å molecular sieves (220 mg) in anhydrous toluene was stirred at RT for 10 minutes, then cis-1,2,3,6-tetrahydrophthalic anhyride (152 mg, 1.0 mmol) was added, after which the mixture was cooled to −27° C. and stirred for another 15 minutes. Trifluoroethanol was added dropwise within 1 minute. The mixture was stirred at that temperature until the starting material was consumed as indicated by TLC (ethyl acetate:hexanes=1:1) analysis (4 h). Aq. HCl (1 N, 10 mL) was added to quench the reaction. The aqueous phase was extracted by 50 mL diethyl ether. The organic phase was washed by aq. HCl (1 N, 2×10 mL), dried with NaSO$_4$ and concentrated to afford the hemiester as a colorless oil (239.7 mg, 95%, 98% ee) without further purification.

Catalyst Recovery

To recover the catalyst QD-(−)-MN, KOH was added to the aqueous layer to adjust the pH value of the solution to 11. The resulting mixture was extracted with ethyl acetate (3×15 mL). The combined organic layer was dried over Na$_2$SO$_4$ and concentrated to afford the catalyst (Quantity, recovery >95%). The recovered catalyst was used for a new batch of alcoholysis of cis-1,2,3,6-tetrahydrophthalic anhyride (1.0 mmol) to give the hemiester in 99% ee and 95% yield.

EXAMPLE 26

Synthesis of N-(1-Adamantyl)chloroacetamide using a Procedure Similar to that Described in *Helv. Chim. Acta* 1988, 71, 1553

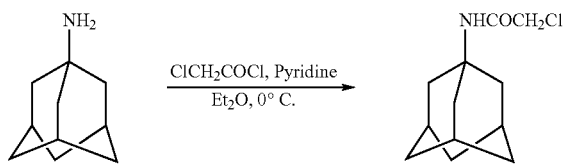

A solution of chloroacetyl chloride (1.6 mL, 20 mmol) in anhydrous diethyl ether (10 mL) was added dropwise within 5 min to a solution of 1-adamantanamine (3.0 g, 20 mmol) and pyridine (1.63 mL, 20 mmol) in anhydrous diethyl ether (40 mL) at 0° C. The yellow suspension was stirred for 1 h at that temperature. The precipitate was removed by filtration and washed by diethyl ether (10 mL). The combined organic solution was washed with HCl (2 N, 2×15 mL), followed by sat. NaHCO$_3$ (15 mL), sat. NaCl (15 mL) solutions and dried with Na$_2$SO$_4$. The solvent was removed at reduced pressure and the residue was recrystallized from diethyl ether-hexanes to afford N-(1-adamantyl)chloroacetamide (1.551 g, 34%) as a yellow solid.

EXAMPLE 27

Synthesis of O-(1-adamantylacetamide)quinidine (Purified by Chromatography)

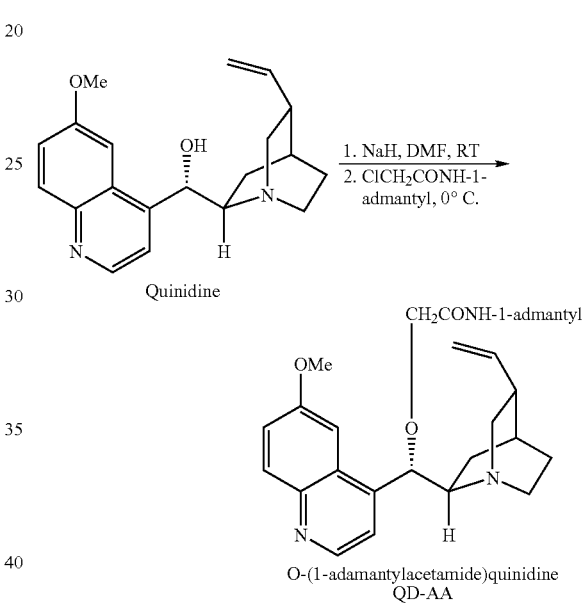

Under a nitrogen atmosphere, NaH (0.12 g, 3.0 mmol, 60% in mineral oil) was washed with hexanes (2×3 mL) and suspended in DMF (10 mL). Quinidine (0.652 g, 2.0 mmol) was added to the mixture in small portions. The reaction mixture was stirred until the solution turned a yellow color (about 2 h). It was then cooled to 0° C. N-(1-adamantyl)chloroacetamide (0.683 g, 3.0 mmol) was added in small portions to the cooled reaction mixture. The reaction mixture was stirred for 2 h at 0° C. and carefully quenched with H$_2$O (14 mL) and then ethyl acetate (14 mL) was added. The organic and aqueous layers were separated. The aqueous phase was extracted with ethyl acetate (2×14 mL). The organic phases were combined, washed with sat. NaHCO$_3$ (14 mL), water (3×14 mL), sat. NaCl (14 mL), dried over Na$_2$SO$_4$, and concentrated under reduced pressure. The brown residue was purified by flash chromatography (ethyl acetate:methanol=9:1) to afford O-(1-adamantylacetamide)quinidine (0.8383 g, 81%) as a white crystalline foam.

1H NMR (CDCl$_3$): δ 1.27-1.39 (m, 1H), 1.48-1.64 (m, 2H), 1.65-1.76 (br, 6H), 1.85 (s, 1H), 1.91-2.07 (m, 1H), 2.02 (s, 6H), 2.07-2.14 (br, 3H), 2.26-2.38 (m, 1H), 2.71-3.27 (m, 5H), 3.81 (s, 2H), 3.96 (s, 3H), 5.05-5.20 (m, 2H), 5.20-5.50

(br, 1H), 5.96-6.07 (m, 1H), 6.30-6.50 (br, 1H), 7.20-7.43 (m, 3H), 8.05 (d, J=9.2 Hz, 1H), 8.77 (d, J=4.8 Hz, 1H).

EXAMPLE 28

Synthesis of 2-Methylpropyl Chloroacetate (See *Helv. Chim. Acta* 1988, 71, 1553)

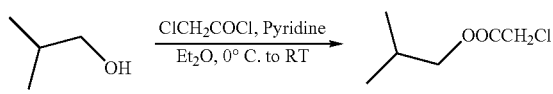

A solution of chloroacetyl chloride (3.2 mL, 40 mmol) in anhydrous diethyl ether (20 mL) was added dropwise within 1 h to a solution of 2-methylpropanol (2.96 g, 40 mmol) and pyridine (3.25 mL, 40 mmol) in anhydrous diethyl ether (80 mL) at 0° C. After warming to RT, the white suspension was stirred for 3 h. The precipitate was removed by filtration and washed by diethyl ether (15 mL). The combined organic solution was washed with HCl (2 N, 30 mL), followed by sat. NaHCO$_3$ (30 mL), sat. NaCl (30 mL) solutions and dried with Na$_2$SO$_4$. Removal of the solvent at about 60 mmHg/30° C. afford 2-Methylpropyl Chloroacetate (5.65 g, 94%) which was used without further purification.

EXAMPLE 29

Synthesis of O-(2-Methylpropylacetate)quinidine (Purified by Chromatography)

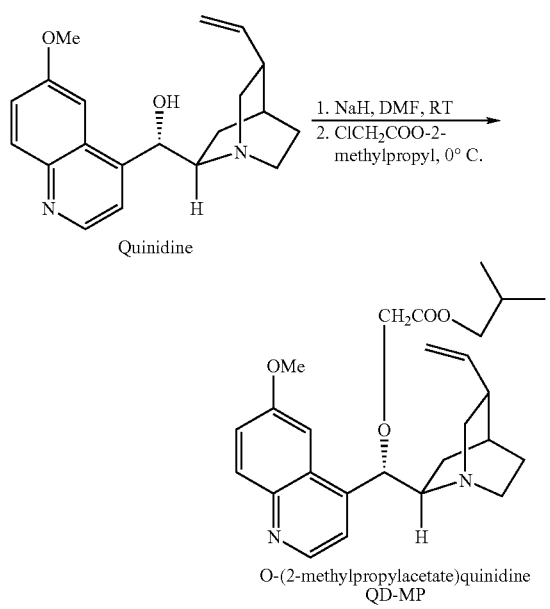

Under a nitrogen atmosphere, NaH (0.12 g, 3 mmol, 60% in mineral oil) was washed with hexanes (2×3 mL) and suspended in DMF (10 mL). Quinidine (0.648 g, 2 mmol) was added to the mixture in small portions. The reaction mixture was stirred until the solution turned a yellow color (about 2 h). It was then cooled to 0° C. 2-Methylpropyl Chloroacetate (0.452 g, 3 mmol) was added dropwise over a 1 min period to the cooled reaction mixture. The reaction mixture was stirred for 4 h at 0° C. and carefully quenched with H$_2$O (14 mL) and then ethyl acetate (14 mL) was added. The organic and aqueous layers were separated. The aqueous phase was extracted with ethyl acetate (2×14 mL). The organic phases were combined, washed with sat. NaHCO$_3$ (14 mL), water (3×14 mL), sat. NaCl (14 mL), dried over Na$_2$SO$_4$, and concentrated under reduced pressure. The brown residue was purified by flash chromatography (ethyl acetate:methanol=9:1) to afford O-(2-methylpropylacetate)quinidine (0.278 g, 32%) as a light brown oil. 1H NMR (CDCl$_3$): δ 0.90 (d, J=6.8 Hz, 6H), 1.22-1.39 (m, 1H), 1.48-1.69 (m, 2H), 1.79-1.86 (br, 1H), 1.86-1.98 (m, 1H), 2.21-2.39 (m, 2H), 2.75-3.22 (m, 4H), 3.44-3.67 (br, 1H), 3.88-4.04 (m, 6H), 4.12 (d, J=16.4 Hz, 1H), 5.08-5.23 (m, 2H), 5.44-5.60 (br, 1H), 6.10-6.24 (m, 1H), 7.32-7.54 (m, 3H), 8.04 (d, J=9.2 Hz, 1H), 8.76 (d, J=4.4 Hz, 1H).

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:
1. A compound represented by formula I:

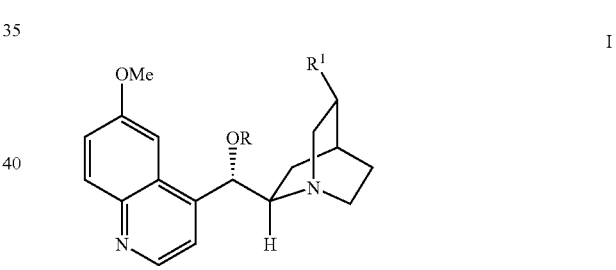

wherein

R represents —C(O)R$^2$, —(C(R$^3$)$_2$)$_n$CO$_2$R$^4$, —(C(R$^3$)$_2$)$_n$C(O)N(R$^5$)$_2$, —(C(R$^3$)$_2$)$_n$CN, —(C(R$^3$)$_2$)$_n$C(O)R$^5$, —C(C(R$^3$)$_2$)$_n$C≡CR$^6$, —(C(R$^3$)$_2$)$_n$OPO(OR$^5$)$_2$, —(C(R$^3$)$_2$)$_n$OR$^5$, —(C(R$^3$)$_2$)$_n$N(R$^5$)$_2$, —(C(R$^3$)$_2$)$_n$SR$^5$, or —(C(R$^3$)$_2$)$_n$NO$_2$;

R$^1$ represents alkenyl;

R$^2$ represents cycloalkyl, or alkenyl;

R$^3$ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R$^4$ represents cycloalkyl, —CH(R$^3$)$_2$, alkenyl, alkynyl, aryl, or aralkyl;

R$^5$ represents independently for each occurrence H, alkyl, alkenyl, aryl, cycloalkyl, or aralkyl;

R$^6$ represents optionally substituted alkyl, alkenyl, aryl, or aralkyl; and n is 1-10.

2. The compound of claim 1, wherein R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, or —C(C(R³)₂)ₙC≡CR⁶.

3. The compound of claim 1, wherein R¹ is —CH=CH₂.

4. The compound of claim 1, wherein R is —C(O)R².

5. The compound of claim 1, wherein R is —(C(R³)₂)ₙCO₂R⁴.

6. The compound of claim 1, wherein R is —(C(R³)₂)ₙCO₂R⁴ and R⁴ is —CH(R³)₂.

7. The compound of claim 1, wherein R is —(C(R³)₂)ₙCO₂R⁴, R⁴ is —CH(R³)₂, n is 1.

8. The compound of claim 1, wherein R is —(C(R³)₂)ₙCO₂R⁴ and R⁴ is cycloalkyl.

9. The compound of claim 1, wherein R is —CH₂CO₂R⁴ and R⁴ is cycloalkyl.

10. The compound of claim 1, wherein R is —CH₂CO₂R⁴, R⁴ is cyclohexyl; and R¹ is —CH=CH₂.

11. The compound of claim 1, wherein R is —CH₂CO₂R⁴; R⁴ is (−)-menthyl, 1-adamantyl, isobornyl, (−)-isopinocamphyl, or (+)-fenchyl; and R¹ is —CH=CH₂.

12. The compound of claim 1, wherein said compound is

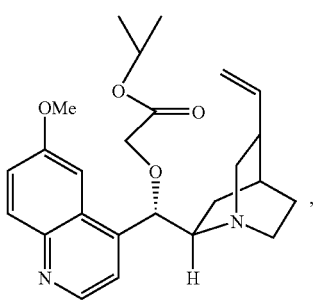

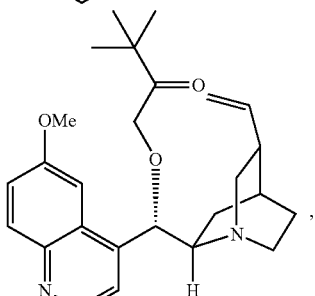

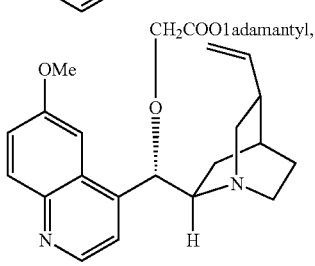

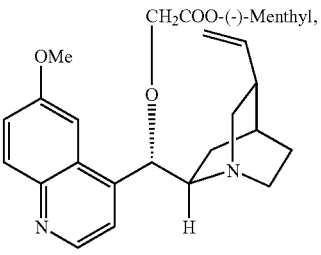

-continued

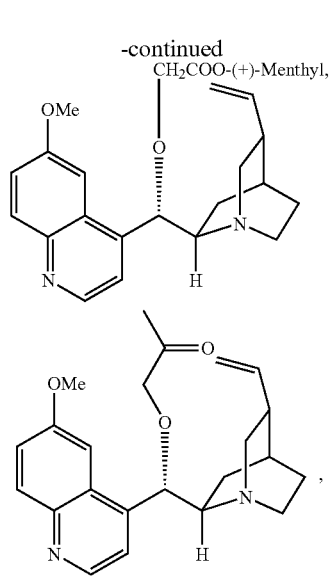

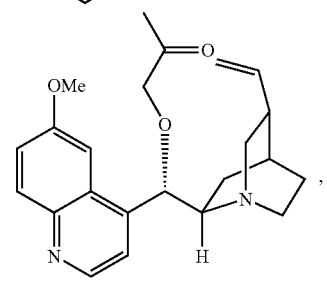

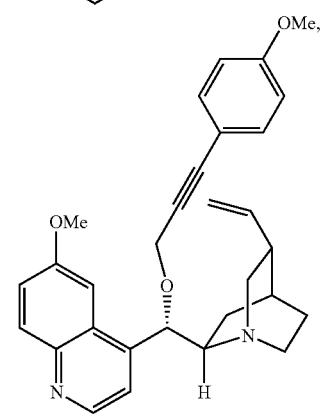

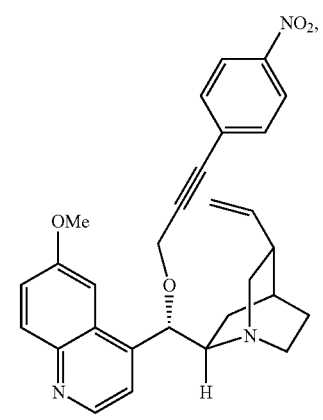

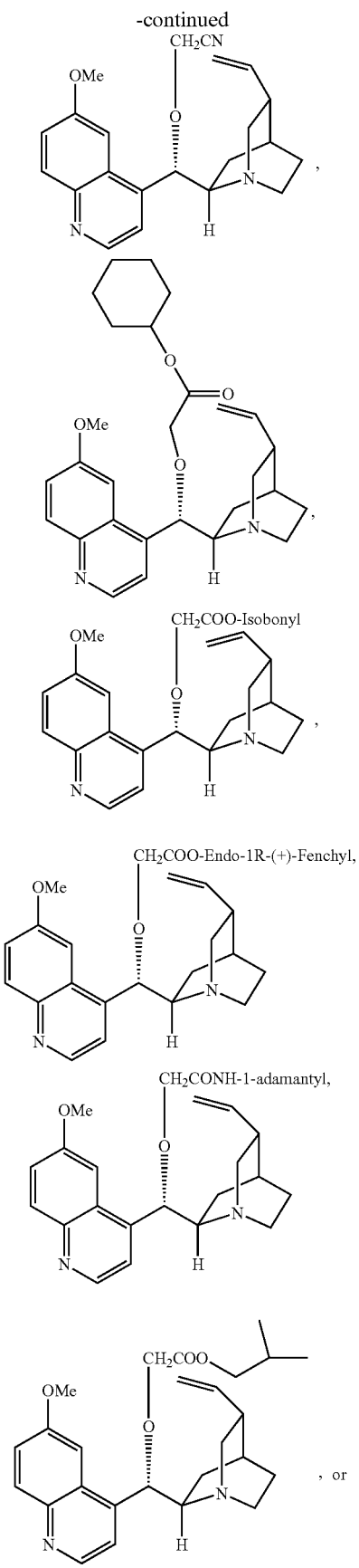
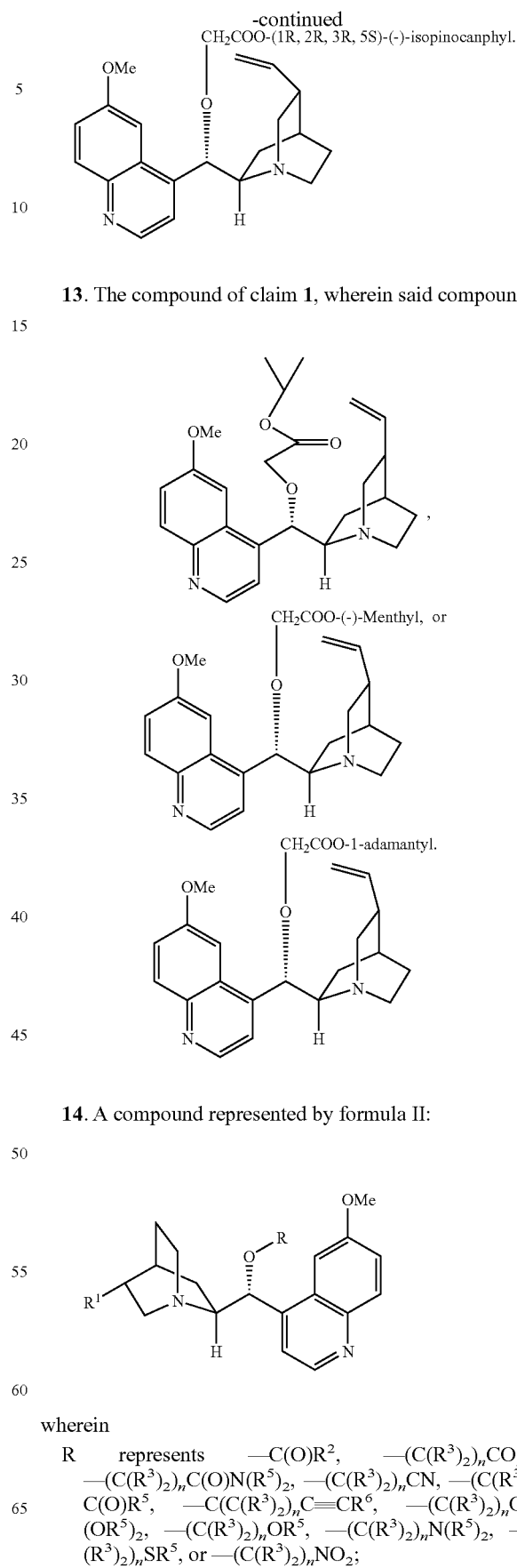
13. The compound of claim 1, wherein said compound is
14. A compound represented by formula II:
$$II$$
wherein
R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, —C(C(R³)₂)ₙC≡CR⁶, —(C(R³)₂)ₙOPO(OR⁵)₂, —(C(R³)₂)ₙOR⁵, —(C(R³)₂)ₙN(R⁵)₂, —(C(R³)₂)ₙSR⁵, or —(C(R³)₂)ₙNO₂;

R¹ represents alkenyl;

R² represents cycloalkyl, or alkenyl;

R³ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

R⁴ represents cycloalkyl, —CH(R³)₂, alkenyl, alkynyl, aryl, or aralkyl;

R⁵ represents independently for each occurrence H, alkyl, alkenyl, aryl, cycloalkyl, or aralkyl;

R⁶ represents optionally substituted alkyl, alkenyl, aryl, or aralkyl; and n is 1-10.

15. The compound of claim 14, wherein said compound represented by formula II is

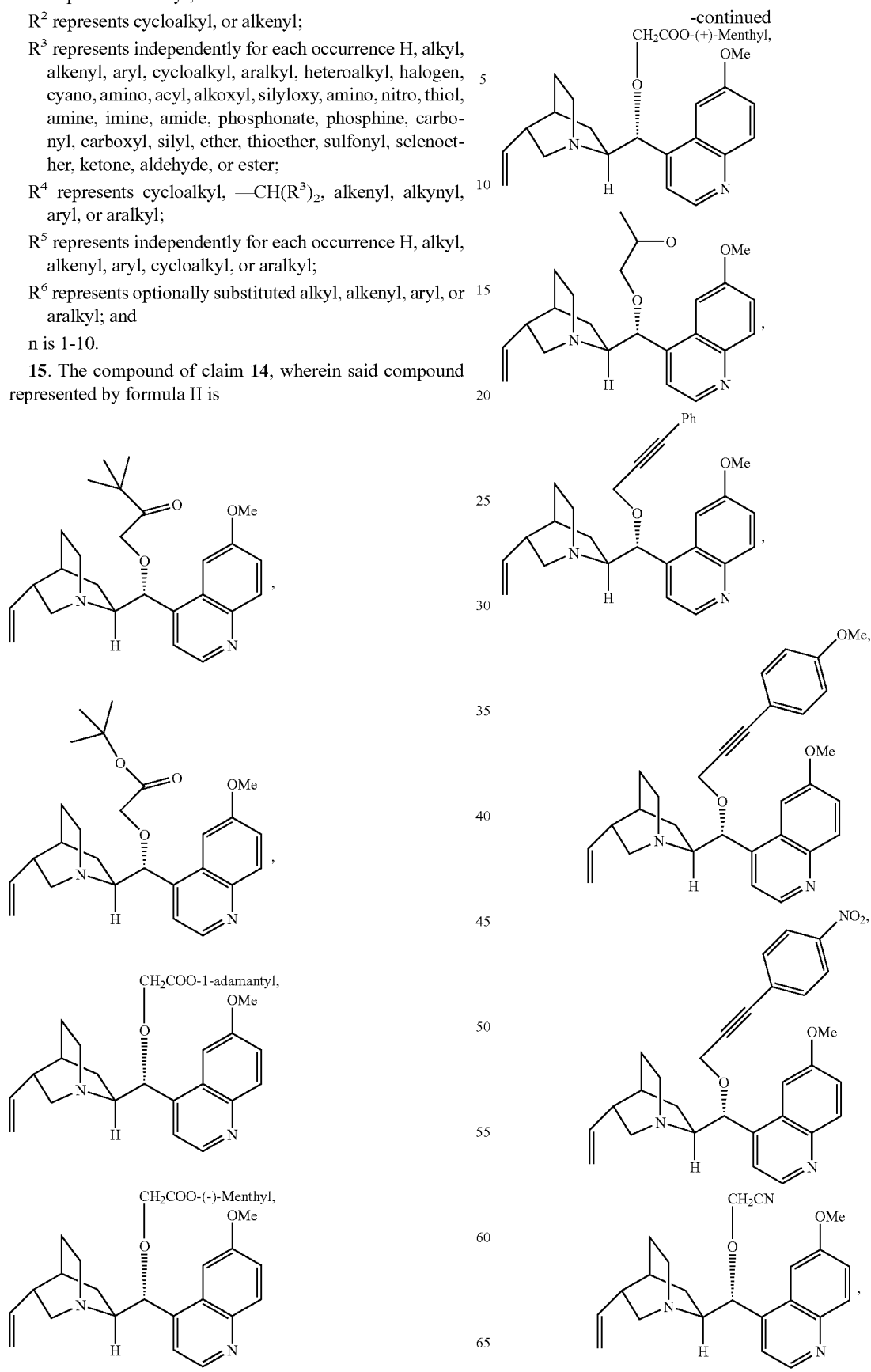

-continued

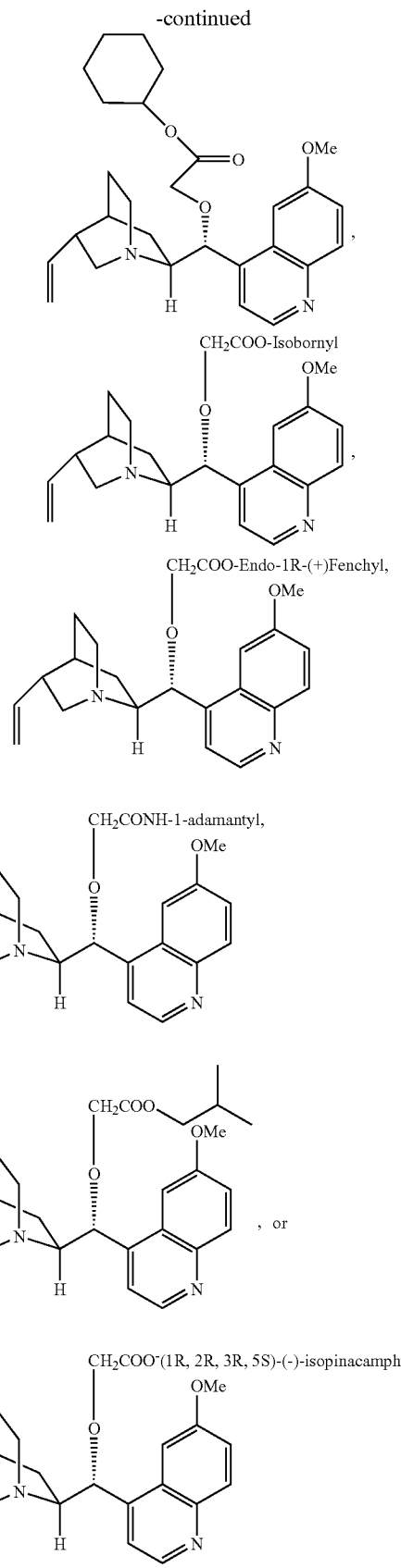

16. A compound represented by formula I:

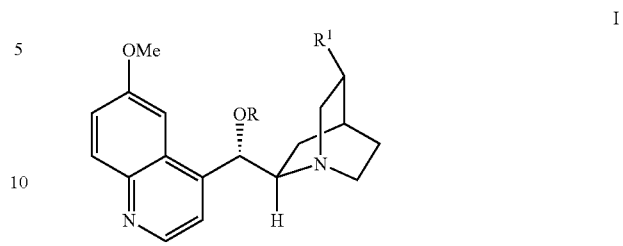

wherein
R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, —C(C(R³)₂)ₙC≡CR⁶, —(C(R³)₂)ₙOPO(OR⁵)₂, —(C(R³)₂)ₙOR⁵, —(C(R³)₂)ₙN(R⁵)₂, —(C(R³)₂)ₙSR⁵, or —(C(R³)₂)ₙNO₂;
R¹ represents alkyl;
R² represents alkenyl;
R³ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphonate, phosphine, carbonyl, carboxyl, silyl, ether, thioether, sulfonyl, selenoether, ketone, aldehyde, or ester;
R⁴ represents cycloalkyl, —CH(R³)₂, alkenyl, alkynyl, aryl, or aralkyl;
R⁵ represents independently for each occurrence H, alkyl, alkenyl, aryl, cycloalkyl, or aralkyl;
R⁶ represents optionally substituted alkyl, alkenyl, aryl, or aralkyl; and n is 1-10.

17. The compound of claim 16, wherein R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R₅, or —C(C(R³)₂)ₙC≡CR⁶.

18. The compound of claim 16, wherein R¹ is ethyl.

19. The compound of claim 16, wherein R is —C(O)R².

20. The compound of claim 16, wherein R is —(C(R³)₂)ₙCO₂R⁴.

21. A compound represented by formula II:

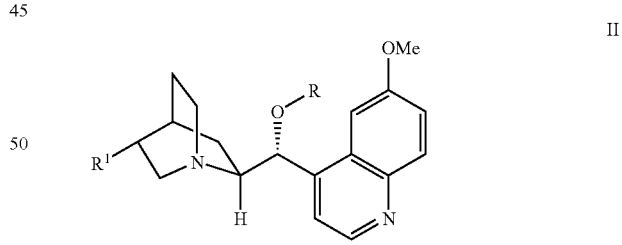

wherein
R represents —C(O)R², —(C(R³)₂)ₙCO₂R⁴, —(C(R³)₂)ₙC(O)N(R⁵)₂, —(C(R³)₂)ₙCN, —(C(R³)₂)ₙC(O)R⁵, —C(C(R³)₂)ₙC≡CR⁶, —(C(R³)₂)ₙOPO(OR⁵)₂, —(C(R³)₂)ₙOR⁵, —(C(R³)₂)ₙN(R⁵)₂, —(C(R³)₂)ₙSR⁵, or —(C(R³)₂)ₙNO₂;
R¹ represents alkyl;
R² represents alkenyl;
R³ represents independently for each occurrence H, alkyl, alkenyl, aryl, cycloalkyl, aralkyl, heteroalkyl, halogen, cyano, amino, acyl, alkoxyl, silyloxy, amino, nitro, thiol, amine, imine, amide, phosphonate, phosphine, carbonyl, carboxyl, silyl, ether, thioether, sulfonyl, selenoether, ketone, aldehyde, or ester;

$R^4$ represents cycloalkyl, —CH($R^3$)$_2$, alkenyl, alkynyl, aryl, or aralkyl;

$R^5$ represents independently for each occurrence H, alkyl, alkenyl, aryl, cycloalkyl, or aralkyl;

$R^6$ represents optionally substituted alkyl, alkenyl, aryl, or aralkyl; and n is 1-10.

22. The compound of claim 21, wherein R represents —C(O)$R^2$, —(C($R^3$)$_2$)$_n$CO$_2$$R^4$, —(C($R^3$)$_2$)$_n$C(O)N($R^5$)$_2$, —(C($R^3$)$_2$)$_n$CN, —(C($R^3$)$_2$)$_n$C(O)$R^5$, or —C(C($R^3$)$_2$)$_n$C≡C$R^6$.

23. The compound of claim 21, wherein $R^1$ is ethyl.

24. The compound of claim 21, wherein R is —C(O)$R^2$.

25. The compound of claim 21, wherein R is —(C($R^3$)$_2$)$_n$CO$_2$$R^4$.

* * * * *